(12) United States Patent
Tremblay et al.

(10) Patent No.: US 8,900,572 B2
(45) Date of Patent: Dec. 2, 2014

(54) MYOGENIC DIFFERENTIATION OF STEM CELLS AND USES THEREOF

(75) Inventors: Jacques P. Tremblay, Stoneham (CA); Sébastien Goudenege, Saint-Lambert (CA); Nicolas B. Huot, Quebec (CA); Carl Lebel, Quebec (CA)

(73) Assignee: Université Laval, Québec (CA)

(*) Notice: Subject to any disclaimer, the term of this patent is extended or adjusted under 35 U.S.C. 154(b) by 59 days.

(21) Appl. No.: 13/523,337

(22) Filed: Jun. 14, 2012

(65) Prior Publication Data

US 2013/0004466 A1   Jan. 3, 2013

Related U.S. Application Data

(60) Provisional application No. 61/496,832, filed on Jun. 14, 2011.

(51) Int. Cl.
A61K 35/12  (2006.01)
C12N 5/077  (2010.01)
A61K 35/54  (2006.01)

(52) U.S. Cl.
CPC .......... *C12N 5/0658* (2013.01); *C12N 2506/02* (2013.01); *C12N 2506/45* (2013.01); *C12N 2799/022* (2013.01); *C12N 2510/00* (2013.01); *C12N 2501/60* (2013.01); *A61K 35/545* (2013.01)
USPC .......................... 424/93.7; 435/366; 435/377

(58) Field of Classification Search
CPC .......... C12N 2506/02; C12N 2506/45; C12N 2510/00; A61K 35/12
USPC ........................................................ 424/93.7
See application file for complete search history.

(56) References Cited

FOREIGN PATENT DOCUMENTS

WO    WO 2010031190 A1 *  3/2010

OTHER PUBLICATIONS

Goudenege et al., Enhancement of myogenic and muscle repair capacities of human adipose-derived stem cells with forced expression of MyoD., Molecular Therapy, vol. 17 No. 6 (Jun. 2009) pp. 1064-1072.*
Huot, Nicolas B., Un adenovirus exprimant MyoD induit la myogenèse des cellules souches embyonnaires humaines. Master's Thesis, Université Laval (2009) pp. 1-81. English translation follows on pp. 82-113.*
Roobrouck et al., Self-renewal and differentiation capacity of young and aged stem cells. Experimental Cell Research, vol. 314 (2008) pp. 1937-1944.*
Wang et al., Reprogramming efficiency and quality of induced pluripotent stem cells (iPSCs) generated from muscle-derived fibroblasts of mdx mice at different ages. PLoS Currents, vol. 3 (Oct. 27, 2011).*
Barberi, T., Bradbury, M., Dincer, Z., Panagiotakos, G., Socci, N. D., and Studer, L. (2007). Derivation of engraftable skeletal myoblasts from human embryonic stem cells. Nat Med 13: 642-648.

(Continued)

*Primary Examiner* — Ruth Davis
*Assistant Examiner* — Kara Johnson
(74) *Attorney, Agent, or Firm* — Goudreau Gage Dubuc; S. Serge Shahinian

(57) ABSTRACT

Disclosed are methods of differentiating stem cells into muscle cells by growing the cells in a myogenic culture medium. The differentiated cells can be used as a source of cells for transplantation in a patient in need thereof.

19 Claims, 16 Drawing Sheets

(56) References Cited

OTHER PUBLICATIONS

Benabdallah, BF, et al. (2008). Inhibiting myostatin with follistatin improves the success of myoblast transplantation in dystrophic mice. Cell Transplant 17: 337-350.

Berkes, C. A., and Tapscott, S. J. (2005). MyoD and the transcriptional control of myogenesis. Semin Cell Dev Biol 16: 585-595.

Brokhman, I., et al. (2009). Genetic modification of human embryonic stem cells with adenoviral vectors: differences of infectability between lines and correlation of infectability with expression of the coxsackie and adenovirus receptor. Stem Cells Dev 18: 447-456.

Collins, C. A., et al. (2009). Integrated functions of Pax3 and Pax7 in the regulation of proliferation, cell size and myogenic differentiation. PLoS ONE 4: e4475.

Darabi, R., et al. (2008). Functional skeletal muscle regeneration from differentiating embryonic stem cells. Nat Med 14: 134-143.

Eiges, R. (2006). Genetic manipulation of human embryonic stem cells by transfection. In Human embryonic stem cell protocols (K. Turksen, Ed.), pp. 221-240. Human Press Inc, New Jersey.

Fujii, I., Matsukura, M., Ikezawa, M., Suzuki, S., Shimada, T., and Miike, T. (2006). Adenoviral mediated MyoD gene transfer into fibroblasts: myogenic disease diagnosis. Brain Dev 28: 420-425.

Gensch, N., Borchardt, T., Schneider, A., Riethmacher, D., and Braun, T. (2008). Different autonomous myogenic cell populations revealed by ablation of Myf5-expressing cells during mouse embryogenesis. Development 135: 1597-1604.

Giordani, J., Bajard, L., Demignon, J., Daubas, P., Buckingham, M., and Maire, P. (2007). Six proteins regulate the activation of Myf5 expression in embryonic mouse limbs. Proc Natl Acad Sci U S A 104: 11310-11315.

Goudenege, S., et al. (2009). Enhancement of Myogenic and Muscle Repair Capacities of Human Adipose-derived Stem Cells With Forced Expression of MyoD. Mol Ther.

Halevy, O., et al. (2004). Pattern of Pax7 expression during myogenesis in the posthatch chicken establishes a model for satellite cell differentiation and renewal. Dev Dyn 231: 489-502.

Huard, J, Tremblay, G, Verreault, S, Labrecque, C, and Tremblay, JP (1993). Utilization of an antibody specific for human dystrophin to follow myoblast transplantation in nude mice. Cell Transplant 2: 113-118.

Itskovitz-Eldor, J., et al. (2000). Differentiation of human embryonic stem cells into embryoid bodies compromising the three embryonic germ layers. Mol Med 6: 88-95.

Kablar, B., Krastel, K., Ying, C., Asakura, A., Tapscott, S. J., and Rudnicki, M. A. (1997). MyoD and Myf-5 differentially regulate the development of limb versus trunk skeletal muscle. Development 124: 4729-4738.

Kitzmann, M., Camac, G., Vandromme, M., Primig, M., Lamb, N. J., and Fernandez, A. (1998). The muscle regulatory factors MyoD and myf-5 undergo distinct cell cycle-specific expression in muscle cells. J Cell Biol 142: 1447-1459.

Kuang, S., and Rudnicki, M. A. (2008). The emerging biology of satellite cells and their therapeutic potential. Trends Mol Med 14: 82-91.

Olguin, H. C., and Olwin, B. B. (2004). Pax-7 up-regulation inhibits myogenesis and cell cycle progression in satellite cells: a potential mechanism for self-renewal. Dev Biol 275: 375-388.

Ozasa, S. et al. (2007). Efficient conversion of ES cells into myogenic lineage using the gene-inducible system. Biochem Biophys Res Commun 357: 957-963.

Park, IH, et al. (2008). Disease-specific induced pluripotent stem cells. Cell 134: 877-886.

Partridge, T. A., Morgan, J. E., Coulton, G. R., Hoffman, E. P., and Kunkel, L. M. (1989). Conversion of mdx myofibres from dystrophin-negative to -positive by injection of normal myoblasts. Nature 337: 176-179.

Rando, TA, and Blau, HM (1994). Primary mouse myoblast purification, characterization, and transplantation for cell-mediated gene therapy. J Cell Biol 125: 1275-1287.

Rudnicki, M. A., Braun, T., Hinuma, S., and Jaenisch, R. (1992). Inactivation of MyoD in mice leads to up-regulation of the myogenic HLH gene Myf-5 and results in apparently normal muscle development. Cell 71: 383-390.

Rudnicki, M. A., Schnegelsberg, P. N., Stead, R. H., Braun, T., Arnold, H. H., and Jaenisch, R. (1993). MyoD or Myf-5 is required for the formation of skeletal muscle. Cell 75: 1351-1359.

Seale, P., Sabourin, L. A., Girgis-Gabardo, A., Mansouri, A., Gruss, P., and Rudnicki, M. A. (2000). Pax7 is required for the specification of myogenic satellite cells. Cell 102: 777-786.

Skuk, D., et al. (2007). First test of a "high-density injection" protocol for myogenic cell transplantation throughout large volumes of muscles in a Duchenne muscular dystrophy patient: eighteen months follow-up. Neuromuscul Disord 17: 38-46.

Smith-Arica, J. R., Thomson, A. J., Ansell, R., Chiorini, J., Davidson, B., and McWhir, J. (2003). Infection efficiency of human and mouse embryonic stem cells using adenoviral and adeno-associated viral vectors. Cloning Stem Cells 5: 51-62.

Sorrentino, V., Pepperkok, R., Davis, R. L., Ansorge, W., and Philipson, L. (1990). Cell proliferation inhibited by MyoD1 independently of myogenic differentiation. Nature 345: 813-815.

Tapscott, S. J., and Weintraub, H. (1991). MyoD and the regulation of myogenesis by helix-loop-helix proteins. J Clin Invest 87: 1133-1138.

Thomson, J. A., et al. (1998). Embryonic stem cell lines derived from human blastocysts. Science 282: 1145-1147.

Trounson, A. (2006). The production and directed differentiation of human embryonic stem cells. Endocr Rev 27: 208-219.

Watanabe, K., et al. (2007). A ROCK inhibitor permits survival of dissociated human embryonic stem cells. Nat Biotechnol 25: 681-686.

Weintraub, H., et al. (1989). Activation of muscle-specific genes in pigment, nerve, fat, liver, and fibroblast cell lines by forced expression of MyoD. Proc Natl Acad Sci U S A 86: 5434-5438.

Zammit, P. S., Golding, J. P., Nagata, Y., Hudon, V., Partridge, T. A., and Beauchamp, J. R. (2004). Muscle satellite cells adopt divergent fates: a mechanism for self-renewal? J Cell Biol 166: 347-357.

Zheng, J. K., et al. (2006). Skeletal myogenesis by human embryonic stem cells. Cell Res 16: 713-722.

Zhu, S., et al. (2009). A small molecule primes embryonic stem cells for differentiation. Cell Stem Cell 4: 416-426.

* cited by examiner

D

A) Mus musculus MyoD1 mRNA. NCBI Reference Sequence: NM_010866.2 (SEQ ID NO:1)

```
   1 aggggccagg acgcccagg acacgactgc tttcttcacc actcctctga caggacagga
  61 cagggaggag gggtagagga cagccggtgt gcattccaac ccacagaacc tttgtcattg
 121 tactgttggg gttccggagt ggcagaaagt taagacgact ctcacggctt gggttgaggc
 181 tggacccagg aactgggata tggagcttct atcgccgcca ctccgggaca tagacttgac
 241 aggcccgac ggctctctct gctcctttga gacagcagac gacttctatg atgaccgtg
 301 tttcgactca ccagacctgc gcttttttga ggacctggac ccgcgcctgg tgcacatggg
 361 agccctcctg aaaccggagg agcacgcaca cttccctact gcggtgcacc caggcccagg
 421 cgctcgtgag gatgagcatg tgcgcgcgcc cagcgggcac caccaggcgg gtcgctgctt
 481 gctgtgggcc tgcaaggcgt gcaagcgcaa gaccaccaac gctgatcgcc gcaaggccgc
 541 caccatgcgc gagcgccgcc gcctgagcaa agtgaatgag gccttcgaga cgctcaagcg
 601 ctgcacgtcc agcaacccga accagcggct acccaaggtg gagatcctgc gcaacgccat
 661 ccgctacatc gaaggtctgc aggctctgct gcgcgaccag gacgccgcgc ccctggcgc
 721 cgctgccttc tacgcacctg gaccgctgcc ccaggccgt ggcagcgagc actacagtgg
 781 cgactcagat gcatccagcc cgcgctccaa ctgctctgat ggcatgatgg attacagcgg
 841 cccccaagc ggccccggc ggcagaatgg ctacgacacc gctactaca gtgaggcggc
 901 gcgcgagtcc aggccaggga agagtgcggc tgtgtcgagc ctcgactgcc tgtccagcat
 961 agtggagcgc atctccacag acagccccgc tgcgcctgcg ctgcttttgg cagatgcacc
1021 accagagtcg cctccgggtc cgccagaggg ggcatcccta agcgacacag aacagggaac
1081 ccagacccg tctcccgacg ccgcccctca gtgtcctgca ggctcaaacc ccaatgcgat
1141 ttatcaggtg ctttgagaga tcgactgcag cagcagaggg cgcaccaccg taggcactcc
1201 tggggatggt gtccctggtt cttcacgccc aaaagatgaa gcttaaatga cactcttccc
1261 aactgtcctt tcgaagccgt tcttccagag ggaagggaag agcagaagtc tgtcctagat
1321 ccagcccaa agaaaggaca tagtcctttt tgttgttgtt gttgtagtcc ttcagttgtt
1381 tgtttgtttt ttcatgcggc tcacagcgaa ggccacttgc actctggctg cacctcactg
1441 ggccagagct gatccttgag tggccaggcg ctcttccttt cctcatagca caggggtgag
1501 ccttgcacac ctaagccctg ccctccacat ccttttgttt gtcactttct ggagccctcc
1561 tggcacccac ttttccccac agcttgcgga ggccactcag gtctcaggtg taacaggtgt
```

```
1621 aaccataccc cactctcccc cttcccgcgg ttcaggacca cttatttttt tatataagac
1681 ttttgtaatc tattcgtgta aataagagtt gcttggccag agcgggagcc ccttgggcta
1741 tatttatctc ccaggcatgc tgtgtagtgc aacaaaaact ttgtatgttt attcctcaag
1801 cgggcgagcc tcgaggctcg ctcgctcagg tgttggaaat aaagacgcta attt
```

B) Mus musculus MyoD protein sequence. NP_034996.2 (SEQ ID NO:2)

MELLSPPLRDIDLTGPDGSLCSFETADDFYDDPCFDSPDLRFFEDLDPRLVHMGALLKPEEHAHFPTAVHP
GPGAREDEHVRAPSGHHQAGRCLLWACKACKRKTTNADRRKAATMRERRRLSKVNEAFETLKRCTSSNPNQ
RLPKVEILRNAIRYIEGLQALLRDQDAAPPGAAAFYAPGPLPPGRGSEHYSGDSDASSPRSNCSDGMMDYS
GPPSGPRRQNGYDTAYYSEAARESRPGKSAAVSSLDCLSSIVERISTDSPAAPALLLADAPPESPPGPPEG
ASLSDTEQGTQTPSPDAAPQCPAGSNPNAIYQVL

C) Homo sapiens MYOD1 protein sequence. NP_002469.2 (SEQ ID NO:3)

MELLSPPLRDVDLTAPDGSLCSFATTDDFYDDPCFDSPDLRFFEDLDPRLMHVGALLKPEEHSHFPAAVHP
APGAREDEHVRAPSGHHQAGRCLLWACKACKRKTTNADRRKAATMRERRRLSKVNEAFETLKRCTSSNPNQ
RLPKVEILRNAIRYIEGLQALLRDQDAAPPGAAAFYAPGPLPPGRGGEHYSGDSDASSPRSNCSDGMMDY
SGPPSGARRRNCYEGAYYNEAPSEPRPGKSAAVSSLDCLSSIVERISTESPAAPALLLADVPSESPPRRQE
AAAPSEGESSGDPTQSPDAAPQCPAGANPNPIYQVL

SEQUENCE LISTING

<160> NUMBER OF SEQ ID NOS: 21

<210> SEQ ID NO 1
<211> LENGTH: 1854
<212> TYPE: DNA
<213> ORGANISM: Mus musculus

<400> SEQUENCE: 1

```
aggggccagg acgcccagg  acacgactgc tttcttcacc actcctctga caggacagga      60
cagggaggag gggtagagga cagccggtgt gcattccaac ccacagaacc tttgtcattg     120
tactgttggg gttccggagt ggcagaaagt taagacgact ctcacggctt gggttgaggc     180
```

```
tggacccagg aactgggata tggagcttct atcgccgcca ctccgggaca tagacttgac      240
aggccccgac ggctctctct gctcctttga gacagcagac gacttctatg atgacccgtg      300
tttcgactca ccagacctgc gctttttttga ggacctggac ccgcgcctgg tgcacatggg      360
```

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Leu Ser Lys Val Asn Glu Ala
            115                 120                 125

Phe Glu Thr Leu Lys Arg Cys Thr Ser Ser Asn Pro Asn Gln Arg Leu
    130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Phe Tyr Ala Pro Gly Pro Leu Pro Pro Gly Arg Gly Ser Glu His Tyr
            180                 185                 190

Ser Gly Asp Ser Asp Ala Ser Ser Pro Arg Ser Asn Cys Ser Asp Gly
            195                 200                 205

Met Met Asp Tyr Ser Gly Pro Pro Ser Gly Pro Arg Arg Gln Asn Gly
    210                 215                 220

Tyr Asp Thr Ala Tyr Tyr Ser Glu Ala Ala Arg Glu Ser Arg Pro Gly
225                 230                 235                 240

Lys Ser Ala Ala Val Ser Ser Leu Asp Cys Leu Ser Ser Ile Val Glu
                245                 250                 255

Arg Ile Ser Thr Asp Ser Pro Ala Ala Pro Ala Leu Leu Leu Ala Asp
            260                 265                 270

Ala Pro Pro Glu Ser Pro Pro Gly Pro Pro Glu Gly Ala Ser Leu Ser
            275                 280                 285

Asp Thr Glu Gln Gly Thr Gln Thr Pro Ser Pro Asp Ala Ala Pro Gln
    290                 295                 300

Cys Pro Ala Gly Ser Asn Pro Asn Ala Ile Tyr Gln Val Leu
305                 310                 315

<210> SEQ ID NO 3
<211> LENGTH: 320
<212> TYPE: PRT
<213> ORGANISM: Homo sapiens

<400> SEQUENCE: 3

Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Met His Val Gly Ala Leu Leu Lys Pro Glu Glu His Ser His
    50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Leu Ser Lys Val Asn Glu Ala
            115                 120                 125

Phe Glu Thr Leu Lys Arg Cys Thr Ser Ser Asn Pro Asn Gln Arg Leu
    130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Pro Pro Gly Ala Ala Ala
            165                 170                 175

Ala Phe Tyr Ala Pro Gly Pro Leu Pro Pro Gly Arg Gly Gly Glu His
            180                 185                 190

Tyr Ser Gly Asp Ser Asp Ala Ser Ser Pro Arg Ser Asn Cys Ser Asp
        195                 200                 205

Gly Met Met Asp Tyr Ser Gly Pro Pro Ser Gly Ala Arg Arg Arg Asn
    210                 215                 220

Cys Tyr Glu Gly Ala Tyr Tyr Asn Glu Ala Pro Ser Glu Pro Arg Pro
225                 230                 235                 240

Gly Lys Ser Ala Ala Val Ser Ser Leu Asp Cys Leu Ser Ser Ile Val
            245                 250                 255

Glu Arg Ile Ser Thr Glu Ser Pro Ala Ala Pro Ala Leu Leu Leu Ala
            260                 265                 270

Asp Val Pro Ser Glu Ser Pro Arg Arg Gln Glu Ala Ala Ala Pro
        275                 280                 285

Ser Glu Gly Glu Ser Ser Gly Asp Pro Thr Gln Ser Pro Asp Ala Ala
    290                 295                 300

Pro Gln Cys Pro Ala Gly Ala Asn Pro Asn Pro Ile Tyr Gln Val Leu
305                 310                 315                 320

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
atttgccaag ctcctgaagc ag                                    22

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ttgatcgctt gcccttctgg                                       20

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
agtgtggatc cagcttgtcc c                                     21

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ttcttgcatc tgctggaggc                           20

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
agtcaagcca agacctgcag g                         21

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
gggagcttgc ttcgaaaacc                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
caagattctt tgccgctacc                           20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ttcagtggga ggtcaggttc                           20

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
gttaagcatt gcaacaagct accc                      24

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
ccaggcttat ctatcatgtg ctatg                     25

<210> SEQ ID NO 14
<211> LENGTH: 23
<212> TYPE: DNA

```
<213> ORGANISM: Artificial Sequence
<220> FEATURE:
<223> OTHER INFORMATION: Synthetic oligonucleotide

<400> SEQUENCE: 14
cgatatacca ggtgctctga ggg                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 15
gggtgggtta cggttacacc tgc                                              23

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
taaggtgtgt aagggaagtc g                                                21

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
ccacagacac atcttccact gt                                               22

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ctgctgaagg agagggagct                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
tgattagctg gtcacacctt                                                  20

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 20 cccctttcatt gacctcaact aca                                             23
```

```
<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
ttgctgatga tcttgaggct gt                                              22
```

US 8,900,572 B2

MYOGENIC DIFFERENTIATION OF STEM CELLS AND USES THEREOF

CROSS REFERENCE TO RELATED APPLICATIONS

This application claims benefit under 35 U.S.C. §119(e), of U.S. provisional application Ser. No. 61/496,832, filed on Jun. 14, 2011 which is incorporated herein in its entirety by reference.

FIELD OF THE INVENTION

The present invention relates to the differentiation of stem cells. More specifically, the present invention is concerned with methods of inducing differentiation of embryonic stem cells (ESCs) and induced pluripotent stem cells (iPSCs) into myogenic cells.

REFERENCE TO SEQUENCE LISTING

Pursuant to 37 C.F.R. 1.821(c), a sequence listing is submitted herewith as an ASCII compliant text file named 13309_25_SeqList.txt, created on Jun. 14, 2012 and having a size of 12 kilobytes. The content of the aforementioned file is hereby incorporated by reference in its entirety.

BACKGROUND OF THE INVENTION

Embryonic stem cells (ESCs) have the ability of self-renewal and are pluripotent, meaning that they can differentiate in any type of cells found in the human body [1]. For these reasons, they hold tremendous potential to treat injuries or degenerative disease since they represent an unlimited source of cells that can be differentiated when desired [2]. One of the diseases for which cell-based therapy is considered promising is Duchenne Muscular Dystrophy (DMD), a lethal X-linked disease caused by a mutation in the dystrophin gene, which results in the absence of this structural protein in myofibers [3]. Due to the considerable amount of myogenic cells required in this kind of cell-based therapy [4], human ESCs represent a promising avenue for the elaboration of such a treatment. However, at the moment the use of hESCs in regenerative medicine is compromised by the small amount of efficient specific lineage differentiation protocols published [5]. In the case of myogenic differentiation, Barberi et al. developed a stroma-free induction system to derive engraftable skeletal myoblasts from hESCs [6]. However this technique had a low conversion rate and was time-consuming.

Thus, there remains a need for providing myogenic cells for transplantation. There remains a need for methods of inducing differentiation of stem cells into myogenic cells.

The present description refers to a number of documents, the content of which is herein incorporated by reference in their entirety.

SUMMARY OF THE INVENTION

The present invention relates to the differentiation of stem cells including embryonic stem cells and induced pluripotent stem cells. More specifically, the present invention is concerned with methods of inducing differentiation of stem cells into myogenic cells.

In accordance with an aspect of the present invention, there is provided a method of inducing differentiation of stem cells in myogenic cells comprising, culturing the cells in a myogenic medium.

Also provided is a method of converting stem cells into multipotent stem cells capable of giving rise to myogenic cells comprising culturing the stem cells in the presence of a myogenic medium.

In another aspect, the present invention provides a method of conditioning stem cells for further differentiation into myogenic cells comprising culturing the cells in a myogenic medium.

In another aspect, the present invention relates to a method of inducing differentiation of stem cells into myogenic cells comprising contacting said cells with a myogenic factor. In an embodiment, the myogenic cells are cells of the skeletal myogenic lineage.

In a further aspect, the invention provides a myogenic cell prepared in accordance with the method of the present invention. In an embodiment, the myogenic cell is for implantation into a subject for increasing muscle mass or preventing or treating a muscle disease, the stem cell having been subjected to a differentiation treatment in a myogenic culture medium, in the presence of a myogenic factor prior to implantation to convert (i.e., transform/differentiate) the stem cell into a myogenic cell. The present invention also concerns a method of transplanting myogenic cells in a subject comprising implanting in the subject myogenic cells prepared in accordance with the present invention.

In another aspect, the invention provides a method of increasing muscle mass or of preventing or treating a muscle disease in a subject comprising implanting into the subject myogenic cells prepared in accordance with the method of the present invention.

In another aspect, the invention provides a use of the myogenic cells prepared according to the method of the invention, for transplantation into a subject.

In another aspect, the invention provides a use of the myogenic cells prepared according to the method of the invention, for increasing muscle mass or preventing or treating a muscle disease in a subject.

In an embodiment the above-noted disease comprises a genetic defect leading to muscle impairment and the myogenic cell comprises a nucleic acid capable of restoring activity corresponding to the genetic defect. In an embodiment, the muscle disease is a dystrophy. In an embodiment the dystrophy is Duchenne Muscular Dystrophy and the nucleic acid encodes dystrophin.

In an embodiment, the myogenic culture medium comprises all amino acids (including L-glutamine), vitamins (Biotin, Folinic Acid, Niacinamide, Panthetonic acid, Riboflavin, Thiamin, Vitamin B12, Pyridoxine, etc.), organic components (e.g., glucose, thymidine, sodium pyruvate, myo-inositol putrescine, adenine, choline chloride, etc.), salts ($CaCl_2$, KCl, $MgSO_4$, NaCl, $Na_2HPO_4$, etc). essential to the growth and/or viability of the cells. In an embodiment, the culture medium comprises basic fibroblast growth factor (bFGF). In an embodiment, the concentration of the bFGF in the myogenic culture medium is between about 0.01 and about 0.5 mg/L. In an embodiment, the concentration of the bFGF in the myogenic medium is about 0.1 mg/L. In an embodiment, the medium comprises insulin. In an embodiment, the concentration of insulin in the myogenic medium is between about 2 and about 8 mg/L. In an embodiment, the concentration of insulin in the myogenic medium is about 5 mg/L.

In an embodiment, the myogenic medium comprises serum. In an embodiment, the concentration of serum in the myogenic medium is between about 0.5% and about 30%. In an embodiment, the concentration of serum in the myogenic medium is between about 10% and about 30%. In an embodiment, the concentration of serum is about 15%. In an embodiment, the concentration of serum in the myogenic medium is low. In an embodiment the low concentration of serum is between about 0.5 and about 5% of serum, in a further embodiment between about 0.5 and about 2% of serum. In an embodiment, the low concentration of serum is about 2%. In an embodiment, the serum is fetal bovine serum (FBS), fetal calf serum (FCS), horse serum or a combination thereof. In an embodiment the culture medium comprises fetal bovine serum. In an embodiment, the medium is substantially the same as the MCM1 medium described herein.

In an embodiment, the above methods comprise culturing the cells in the presence of at least one (i.e., one or more) myogenic factor. In an embodiment, the at least one myogenic factor is selected from MyoD (Gene ID 4654, encoding NP_002469.2), Pax3 (Gene ID 5077 encoding NP_000429.2; NP_001120838.1; NP_039230.1; NP_852122.1; NP_852124.1; NP_852125.1 and/or NP_852126.1), Pax7 (Gene ID 5081 encoding NP_001128726.1; NP_002575.1; NP_039236.1), Myf5 (Gene ID 4617 encoding NP_005584.2), and myogenin (Gene ID 4656 encoding NP_002470.2). In an embodiment, the at least one myogenic factor is a functional derivative of a myogenic factor noted above or a nucleic acid encoding same. In an embodiment, the functional derivative is an allelic variant. In an embodiment, the myogenic factor is MyoD. In an embodiment, the MyoD factor encodes a MyoD protein as set forth in SEQ ID NO:3 or a functional derivative of the MyoD protein of SEQ ID NO:3. In an embodiment, the functional derivative is an allelic variant.

In accordance with an aspect of the present invention, the myogenic factor can be provided to the stem cells by i) Treating said cells with a myogenic factor protein; ii) Inducing said myogenic factor expression in said cells; or iii) Introducing in said cells a nucleic acid capable of expressing the myogenic factor. In an embodiment, the myogenic factor is provided by introducing in the cells a nucleic acid capable of expressing the myogenic factor. In an embodiment, the myogenic factor is a nucleic acid encoding MyoD.

In an embodiment, the nucleic acid encoding the myogenic factor of the present invention is introduced into said cells using an adeno-associated viral vector; a retroviral vector, a lentiviral vector, a non-integrative lentiviral vector or a non-viral vector. In an embodiment, the vector is an adeno-associated viral vector. In another embodiment, the vector is a lentiviral vector.

In an embodiment, the above mentioned method comprises first growing said stem cells in a proliferation culture medium. In an embodiment, the proliferation medium is substantially the same as the myogenic medium. In an embodiment, the proliferation medium is different from the myogenic culture medium. Preferably, the proliferation culture medium comprises a concentration of serum that is higher than the concentration of serum in the myogenic culture medium. In an embodiment, the proliferation medium is substantially the same as the MCM1 medium described herein. In an embodiment, the proliferation medium comprises between about 10% and about 30% of serum. In an embodiment, the serum is fetal bovine serum (FBS), fetal calf serum (FCS), horse serum or a combination thereof. In an embodiment the culture medium comprises fetal bovine serum. In an embodiment, the method further comprises culturing the cells in a fresh culture medium comprising low levels of serum prior to transplantation. In an embodiment the culture medium is DMEM.

Stem cells that can be used in accordance with the present invention include embryonic stem cells, pluripotent stem cells and multipotent progenitor cells. In an embodiment, the pluripotent cells are induced pluripotent stem cells (iPSCs). In an embodiment, the stem cells are mammalian stem cells. In an embodiment, the stem cells are human stem cells. In an embodiment, the stem cells are iPSCs derived from a subject suffering from Duchenne muscular dystrophy.

In an embodiment, the stem cells express CD73 and at least one of Rex-1, OCT4, SOX2 and Nanog.

In an embodiment, the method of the present invention further comprises selecting CD73 positive stem cells prior to culturing or growing the cells in a myogenic culture medium. In an embodiment, the selection of CD73 cells is performed by isolating CD73 positive cells by FACS. In an embodiment, the method comprises growing or culturing the stem cells as single cells (as opposed to colonies). This is preferable when the method comprises introducing a nucleic acid encoding a myogenic factor in the cells, especially, when the nucleic acid is comprised in viral particles.

Myogenic cells prepared in accordance with the present invention express at least one, at least two, at least three, at least 4, at least 5 and preferably all of the following myogenic markers: Pax3, Pax7, MyoD, myogenin, CD56, desmin and MHC. In an embodiment myogenic cells prepared in accordance with the present invention express at least Myogenin, MyoD and MHC. In an embodiment, the myogenic cells of the present invention express lower levels of Rex-1, OCT4, SOX2 and/or Nanog than stem cells which have not been treated in accordance with the method of the present invention.

In an embodiment, the myogenic culture medium induces the expression of TBX1 and TBX4 in stem cells.

Myogenic cells prepared in accordance with the present invention can be used for transplantation. In an embodiment, the myogenic cells prepared in accordance with the present invention are autologous to the subject which will receive the transplantation.

In another aspect, the present invention provides a method of inducing differentiation of stem cells into myogenic cells comprising inducing MyoD expression in said cells. In an embodiment, the method comprises introducing in the cells a nucleic acid capable of expressing the myogenic gene MyoD. In an embodiment, the MyoD gene encodes for a MyoD protein comprising SEQ ID NO:3 or a functional derivative of the MyoD protein of SEQ ID NO:3. In an embodiment, the functional derivative is an allelic variant.

The invention further provides a composition comprising the above-noted myogenic cells and a suitable carrier, such as a pharmaceutically acceptable or biocompatible carrier. In an embodiment, the carrier is adapted for the implantation, transplantation or transfer of said cells into a subject.

As used herein "pharmaceutically acceptable carrier" or "excipient" includes any and all solvents, dispersion media, coatings, antibacterial and antifungal agents, physiological media, and the like that are physiologically compatible. In embodiments the carrier is suitable for intravenous or intramuscular administration. Pharmaceutically acceptable carriers include sterile aqueous solutions or dispersions and sterile powders for the extemporaneous preparation of sterile injectable solutions or dispersion. The use of such media and agents, such as for the implantation of cells, is well known in the art. Except insofar as any conventional media or agent is incompatible with a cell of the invention, use thereof in the compositions of the invention is contemplated.

The invention further provides a package comprising the reagents and instructions for the preparation of the above-noted myogenic cells. For example, the package may comprise a suitable culture medium, together with instructions for culturing stem cells under conditions to obtain a myogenic cell suitable for transplantation.

As used herein, the term stem cells refers to cells capable of differentiating into many cell types of an organism from which it arises and includes totipotent, pluripotent and multipotent cells (e.g., stem cells of embryonic origin (e.g., ESCs), induced stem cells (iPSCs) and multipotent progenitor cells).

As used herein, the expression "pluripotent stem cells" is meant to refer to cells having the potential to differentiate into any of the three germ layers: endoderm (interior stomach lining, gastrointestinal tract, the lungs), mesoderm (muscle, bone, blood, urogenital), or ectoderm (epidermal tissues and nervous system). Pluripotent stem cells can give rise to any fetal or adult cell type, including muscle tissue. However, alone they cannot develop into a fetal or adult organism because they lack the potential to contribute to extraembryonic tissue, such as the placenta. The expression "Pluripotent stem cells" includes stem cells of adult, infant (cord blood) or embryonic origin as well as induced pluripotent stem cells.

Induced pluripotent stem cells, commonly abbreviated as iPS cells or iPSCs are a type of pluripotent stem cell artificially derived from a non-pluripotent cell, typically an adult somatic cell, by inducing a "forced" expression of specific genes. iPSCs are pluripotent (or multipotent) and can differentiate into several cell types including myogenic cells. In an embodiment, the iPSCs used in accordance with the present invention are of human origin. In an embodiment, the iPSCs are derived from a fibroblast of a Duchenne Muscular Dystrophy patient.

As used herein, "Multipotent progenitor cells" have the potential to give rise to cells from multiple, but limited number of lineages. An example of a multipotent stem cell is a mesenchymal stem cell which can differentiate into osteoblasts, chondrocytes, muscles cells and other cell types.

Stem cells of the present invention can be derived from any organisms. Preferably, the stem cells of the present invention are of mammalian origin and more preferably of human origin. In embodiments, the cell may be autologous or heterologous to the subject in which it is transferred. In a further embodiment, the cell may be allogeneic to the subject.

As used herein, the term "myogenic cells" refers to cells giving rise to or forming muscle tissue and includes cells expressing one or more of the following markers Pax3, Pax7, MyoD, myogenin and MHC and low levels of embryogenic markers such as Rex-1. In an embodiment, myogenic cells of the present invention are capable of fusing and forming myotubes comprising 10, preferably between 5 and 20 and more preferably at least 20 nuclei.

As used herein, the term "myogenic medium" refers to a medium capable of supporting the differentiation of cells (e.g., stem cells, pluripotent stem cells, multipotent progenitor cells, etc.) into myogenic cells. In an embodiment, the myogenic medium is MCM1. In an embodiment, the myogenic medium comprises low concentration of serum (e.g., about 0-5% serum). The myogenic medium may serve as a proliferation medium in which the cells are first grown in order to obtain a desired amount of cells as well as a differentiation medium, which serves to terminally differentiate the cells into myogenic cells. In an embodiment, the proliferating medium is different from the differentiation medium. In an embodiment, the proliferating medium is a myogenic medium comprising between about 10 and about 30% serum, preferably 15% of serum. In an embodiment, the proliferating medium is MTESR1. In an embodiment, the differentiation medium is a myogenic medium comprising between about 0 and about 5% of serum.

As used herein the term "allelic variant" defines a naturally occurring alternative form of a gene which occupies a given locus on a chromosome. The allelic variation may or may not be reflected in the encoded protein. The allelic variants of the present invention are functional derivatives of the wild type allele (i.e., that it provides the same muscular function as the wild-type protein; e.g., MyoD as set forth in SEQ ID NO:3) and excludes non-functional naturally occurring variants e.g., large deletion mutants or other mutants devoid of biological activity.

As used herein, the designation "functional derivative" denotes, in the context of a functional variant of a sequence whether a nucleic acid or amino acid sequence, a molecule that retains a biological activity that is substantially similar to that of the original sequence. This functional variant or equivalent may be a natural derivative or may be prepared synthetically. Such derivatives include amino acid sequences having substitutions, deletions, or additions of one or more amino acids, provided that the biological activity of the protein is conserved. The same applies to variants of nucleic acid sequences which can have substitutions, deletions, or additions of one or more nucleotides, provided that the biological activity of the sequence is generally maintained. When relating to a protein sequence, the substituting amino acid generally has chemico-physical properties which are similar to that of the substituted amino acid. The similar chemico-physical properties include similarities in charge, bulkiness, hydrophobicity, hydrophylicity and the like. Conserved amino acid substitutions are known to the skilled artisan. The term "functional derivatives" is intended to include "functional fragments", "functional segments", "functional variants", "functional analogs" or "functional chemical derivatives" of the subject matter of the present invention.

In embodiments, polypeptides and nucleic acids which are substantially identical or homologous to those noted herein may be utilized in the context of the present invention.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with any of MyoD (encoding SEQ ID NO:2 or SEQ ID NO:3), Pax3 (Gene ID 5077 encoding NP_000429.2; NP_001120838.1; NP_039230.1; NP_852122.1; NP_852124.1; NP_852125.1 and/or NP_852126.1), Pax7 (Gene ID 5081 encoding NP_001128726.1; NP_002575.1; NP_039236.1), Myf5 (Gene ID 4617 encoding NP_005584.2), and myogenin (Gene ID 4656 encoding NP_002470.2).

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, J. Mol. Biol. 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny or cell or genome with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

In another aspect of the invention, an isolated nucleic acid, for example a nucleic acid sequence encoding a peptide compound of the invention, or homolog, fragment or functional derivative thereof, may further be incorporated into a recombinant expression vector. In an embodiment, the vector will comprise transcriptional regulatory sequences or a promoter operably-linked to a nucleic acid comprising a sequence capable of encoding a peptide compound, polypeptide or domain of the invention. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of protein coding sequences with which they are operably-linked.

The recombinant expression vector of the present invention can be constructed by standard techniques known to one of ordinary skill in the art and found, for example, in Sambrook et al. (1989) in Molecular Cloning: A Laboratory Manual. A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation and selection in bacteria and host cells. In addition, the vectors of the present invention may comprise a sequence of nucleotides for one or more restriction endonuclease sites. Coding sequences such as for selectable markers and reporter genes are well known to persons skilled in the art.

A recombinant expression vector comprising a nucleic acid sequence of the present invention may be introduced into a host cell, which may include a living cell capable of expressing the protein coding region from the defined recombinant expression vector. The living cell may include both a cultured cell and a cell within a living organism. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals. Methods for introducing DNA into mammalian cells in vivo are also known, and may be used to deliver the vector DNA of the invention to a subject for gene therapy for a muscle disease.

The articles "a," "an" and "the" are used herein to refer to one or to more than one (i.e., to at least one) of the grammatical object of the article.

The use of the word "a" "an" and "the" when used in conjunction with the term "comprising" in the claims and/or the specification may mean "one" but it is also consistent with the meaning of "one or more", "at least one", and "one or more than one". The singular forms "a", "an" and "the" include corresponding plural references unless the context clearly dictates otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps and are used interchangeably with, the phrases "including but not limited to".

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range.

BRIEF DESCRIPTION OF THE DRAWINGS

In the appended drawings:

FIG. 1A: The H9 cell colonies had the morphological characteristics of undifferentiated hESCs. They formed monolayer colonies with defined borders and the ratio nucleus/cytoplasm was high. FIG. 1B: Hoescht staining of hESC colonies. FIG. 1C: Results of a FACS analysis complemented the morphological observation. The Stage-specific embryonic antigen-4 (SSEA4) staining indicated that 95% of the H9 cells were in an undifferentiated state, confirming the morphological observation. FIG. 1D: The expression of the SSEA4 marker in the colonies was confirmed by immunohistochemistry. FIG. 1E No Myosin Heavy Chain (MHC) expression was detected by immunocytochemistry. FIG. 1F: MHC immunochemistry of the positive control (myoblasts after 4 days in differentiation medium. MHC positive cells appear as long red filaments. Scale bars are respectively 400 µm in A, and 120 µm in B, D, E and F.

FIG. 2A: Morphological changes were observed in the hESCs 24 h after infection regardless of the presence of the transgene in the adenovirus. This change may be attributed to the use of a medium which did not contain the growth factors necessary for the maintenance of the undifferentiated state. Colonies started to lose their definite boundary and the cytoplasm of cells expanded. FIG. 2B: Five days following an Ad.CAG-MyoD infection, only a few cells of the colony stained positive for MyoD. FIG. 2C: The number of cells entering the myogenic pathway, based on the desmin staining in light green (ex. Arrows), was even lower than the amount of MyoD positive cells at the same viral concentration (same than in FIG. 2B). However, these desmin positive cells were only observed when the hESCs were infected with the Ad.CAG-MyoD and none were detected in the GFP control. The 200 µm bar applies to A, B, and C.

FIG. 3A: Dose dependent expression of control GFP was observed 5 days after infection with Ad.CAG-GFP in single cells. FIG. 3B: Positive cells were observed at a MOI (Multiplicity of Infection i.e., ratio of infectious agents (virus) to infection targets (cells)) as low as 1 and almost 100% of the hESCs infected with Ad.CAG.MyoD stained positive for MyoD at a MOI of 30 FIG. 3C: An increase in desmin expression was observed 5 days after infection with the Ad.CAG-MyoD construct at MOI of 0 to 30. Higher MOI did not result in a better myogenesis of the hESCs and increased cell mortality. These results correlated with the minimal amount of virus needed to obtain 100% of the transgene expression. FIG. 3D: Immunochemistry for MHC after infection of isolated hESCs with the Ad.CAG-MyoD and cultured in low serum. 20±3% of the Ad.CAG.MyoD infected hESCs expressed the MHC in the differentiation medium (i.e., under low serum (2%) conditions). The majority of the MHC positive cells (left panels) remained mononucleated and only a few myotubes containing only 2 to 5 nuclei were observed and the majority of the MHC-positive cells grew as single cells and were not able to form multinucleated myotubes. The nuclei were stained with DAPI (center column). Scale bars ar respectively 100 µm in A and D and 50 µm in B.

FIG. 6 shows a FACS analysis of hESC-derived mesenchymal-like precursors generated under MCM1 culture conditions.

FIG. 7A: Hoescht staining of MCM1-hESCs. FIG. 7B: Immunocytochemistry confirmed the loss of embryonic marker SSEA4. FIG. 7C: Myosin Heavy Chain (MHC) was not detected even after 2 weeks in differentiation medium (MCM1, low serum condition). FIG. 7D: MHC immunocytochemistry of positive control (myoblasts after 5 days in differentiation medium). The scale bar is 120 µm for A and D.

(FIG. 10A) or dystrophic MCM1-MyoD-hiPSCs (FIG. 10B) and immunostained for human spectrin. The presence of MCM1-MyoD-hESCs derived muscle fibers was further confirmed by co-labeling of most of the human spectrin-positive fibers (FIG. 10C, right panel) with human-specific anti-dystrophin (FIG. 10C, left panel). Representative cross-sections of Rag/mdx TA muscles injected intramuscularly with 0.5 million MCM1-MyoD-hESCs and cardiotoxin (FIG. 10D) at several sites (10-15) throughout each muscle. The number of human spectrin positive muscle fibers per muscle section was counted for the 3 best sections of each grafted muscle. The * indicates statistically different results between the muscle grafted with myoblasts and those grafted with MCM1-MyoD-hiPSCs (n=7, p<0.05) (FIG. 10E). Scale bars are respectively 120 µm in A, B and D and 40 µm in C.

FIG. 12 shows: A) the murine MyoD mRNA sequence (SEQ ID NO:1); b) the murine MyoD protein sequence (SEQ ID NO:2); and c) the human MyoD protein sequence (SEQ ID NO:3).

DESCRIPTION OF ILLUSTRATIVE EMBODIMENTS

Figure 1:
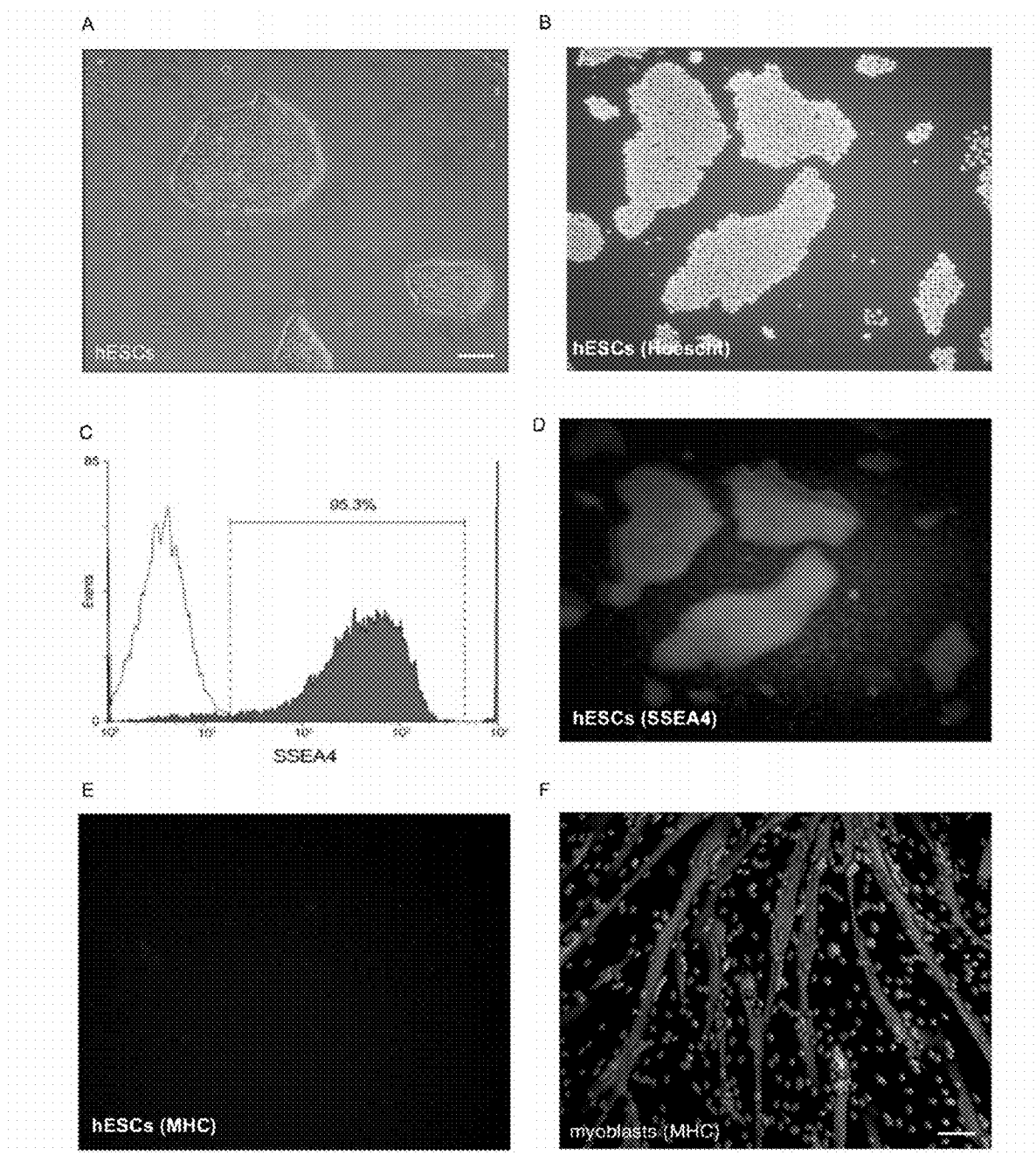
FIG. 1 shows the characteristics of the H9 hESCs.

Human embryonic stem cells (hESCs) and Induced Pluripotent Stem cells (hiPSCs) have an endless self-renewal capacity and can differentiate into all types of cells found in the body. For this reason, they represent an unlimited source of cells for cell therapy of degenerative diseases, such as Duchenne muscular dystrophy. Due to the considerable amount of myogenic cells required in this kind of cell-based therapy, hESC and hiPSCs represent a promising avenue for the elaboration of such a treatment. However, at the moment the use of hESCs and hiPSCs in regenerative medicine is compromised by the small amount of efficient specific lineage differentiation protocols published. In the case of myogenic differentiation, Barberi & al developed a stroma-free induction system to derive engraftable skeletal myoblasts from hESCs. However this technique had a low conversion rate was and was time consuming. Since this work published in 2006, no major advance has emerged in this area.

The instant inventors have developed a new protocol to differentiate hESCs and dystrophic hiPSCs into skeletal muscle combining for example an adenovirus expressing the master gene MyoD under for example the CAG promoter (Ad.CAG-MyoD) and a myogenic culture medium (e.g., MCM1). The results described herein indicate that the combination of MCM1 medium and adenovirus expression is a useful protocol for hESCs and dystrophic hiPSCs differentiation into skeletal muscle cells. The fusion potential of these cells was established by the formation of multinucleated myotubes i.e. The Applicants have shown that 60% of the nuclei located in myotubes stained positive for myosin heavy chain. The potential of these cells to fuse with muscle fibers in vivo was also demonstrated by human spectrin positive fibers. hESCs or hiPSCs differentiated into myogenic cells of the present invention can be used as an alternative source of cells for basic applications as well as for transplantation in subjects in need thereof.

The present inventors have determined that infection with an adenovirus coding for MyoD leads to the differentiation of hESC and dystrophic hiPSC in myogenic cells. The differentiation of hESC and dystrophic hiPSC into myogenic cells can be further increased by culturing the cells in the myogenic medium MCM1. The myogenic capacity of myogenic cells derived from hESCs or dystrophic hiPSCs was demonstrated by the formation of multinucleated myotubes. 60% of the nuclei located in myotubes stained positive for the myosin heavy chain. RT-PCR analysis indicated that MCM1 medium and MyoD induced the expression of several myogenic genes. The cells did not show karyotype abnormalities after these treatments. The potential of these cells to fuse with muscle fibers in vivo was demonstrated by the formation of muscle fibers expressing human spectrin. hESCs or hiPSCs differentiated into muscles cells in accordance with the method of the present invention can be used as an alternate source of cells in muscle cell transplantation for the treatment of muscle diseases such as DMD.

Thus, described herein is a rapid and effective two steps procedure. The first step is to transfer the hESCs in a myogenic medium. This induced a mesenchymal-like differentiation (i.e., formation of CD73+ cells). The second step is an infection of the stem cells with an adenovirus expressing MyoD under the ubiquitous promoter CAG (Ad.CAG-MyoD). Results indicate that with this protocol, the hESCs differentiated in cells expressing genes and proteins specific of muscle precursor cells. The conversion was so effective that a selection of the myogenic cells was not necessary to obtain very good fusion not only in vitro but also with the host muscle fibers following intramuscular injections and to avoid the formation of teratomas by the non-myogenic cells. Our procedure also permitted to convert hiPSCs obtained from a DMD patient inmyogenic cells, which formed abundant muscle fibers expressing human spectrin following their transplantation in immunodeficient Rag/mdx mice.

The following examples are illustrative of various aspects of the invention, and do not limit the broad aspects of the invention as disclosed herein.

Example 1

Materials and Methods

Reagents

The reagents were purchased from the following companies: FBS from Biomedia (Drummonville, Québec, Canada); penicillin/streptomycin, trypsin from Gibco (Burlington, Ontario, Canada); MATRIGEL from BD Biosciences (Mississauga, Canada); MTESR1 media and dispase from Stem Cell Technologies (Vancouver, BC, Canada); MB1 medium from Hyclone-Logan (Logan, USA), random primers, Go Tag, Oligo(dT) and RNasin from Promega (WI, USA); mouse monoclonal anti-β chain of spectrin (NCLSPEC1) antibody from Novocastra (Newcastle upon Tyne, UK); mouse anti-MyoD (CS-304) from Santa Cruz; anti-human Myosin Heavy Chain (MHC, Mab 4470) from R&D System; mouse anti-human desmin (clone D33, cat. Nb. M0760) from DAKO (Burlington, Ontario, Canada); mouse anti-SSEA4 (clone MC813, cat Nb. ab16287) from abeam-Abeam (Cambridge, Mass., USA); mouse anti-human CD73 conjugated with APC (clone AD2, Cat Nb. 17-0739-42) from ebioscience (San Diego, Calif., USA); mouse anti CD56 conjugated with PE (Cat. No. 340685) from BD Biosciences (Mississauga, Canada); goat anti-mouse IgG conjugated with ALEXA FLUOR 546, goat anti-mouse IgG conjugated with ALEXA FLUOR 488 from Molecular probes (Eugene, Oreg.); mouse mAb for human and dog dystrophin MANDYS104 from CIND (Oswestry, UK); goat anti-mouse biotinylated antibody from DAKO diagnostics (Mississauga, ON, Canada); DAB Substrate Kit for detection of horseradish peroxidase (HRP) activity from Vector laboratories (Burlington, Ontario, Canada); CYQUANT cell proliferation assay kits from Molecular Probes; the ROCK inhibitor Y-27632 from VWR (Mississauga, Canada); the Cardiotoxin and all the other products from Sigma-Aldrich (St. Louis, Mo.). conjugated with PE (Cat. No. 340685)

Animals

All the experiences were approved by the animal care committee of the CHUL (Centre Hospitalier de l'Université Laval). Mdx mice (dystrophic mouse model with dystrophinopathy on a C57BL10J genetic background) were purchased from Jackson laboratory and reproduced in our animal facility. The Rag/mdx mice were produced in our laboratory by crossing mdx mice with Rag −/− mice. The experiments with the hESCs and hiPSCs were authorized by the Stem Cell Oversight Committee of Canada (SCOC).

hESCs Culture

A H9 cell line was obtained from WiCell Research Institute (Madison Wis.). The undifferentiated cells were grown on MATRIGEL (BD Biosciences)-coated Petri dishes using the MTESR1 medium (Stem Cell Technologies) as described by Ludwig et al. [35]. The cells were enzymatically passaged every 5 to 7 days using 1 mg/ml of dispase. For mesenchymal differentiation, the culture medium of hESCs still on MATRIGEL was changed for MCM1, the culture medium that is normally used for the proliferation of human myoblasts. After 4 to 6 days in MCM1 medium, hESCs were trypsinized to a single-cell suspension and plated on three MATRIGEL free 6 wells plate. Before confluence, cells were trypsinized and plated in one T25 or T75 flask (MCM1-hESCs). Only when a large number of cells was required for intra-muscular transplantation, the MCM1-hESCs were proliferated for an additional 3 to 4 passages, this required about 2 weeks. The cells were then infected or not with Ad.CAG-MyoD (MOI 30) at 60% confluence.

Dystrophic hiPSCs Culture

The dystrophic hiPSCs cell line was obtained from Daley laboratory. The cells were grown on MATRIGEL (BD Biosciences)-coated Petri dishes using the MTESR1 media (Stem Cell Technologies). The cells were enzymatically passaged every 5 to 7 days using 1 mg/ml of dispase (Stem Cell Technologies). The dystrophic hiPSC cell line was bought from Georges Daley laboratory (Harvard Univ., Boston, USA). The derivation of these cells from skin fibroblasts has been previously described [36]. The cells were grown on MATRIGEL coated Petri dishes using the MTESR1 media. The undifferentiated cells were enzymatically passaged every 5 to 7 days using 1 mg/ml of dispase. For mesenchymal-like differentiation, hiPSCs were grown in the MCM1 medium. After 5 days in MCM1 medium, the hiPSCs were trypsinized to a single-cell suspension and plated on three MATRIGEL free 6 wells plate. Before confluence, cells were trypsinized and plated in one T75 flask (MCM1-hiPSCs). The cells were then infected or not with Ad.CAG-MyoD (MOI 30) at 60% confluence.

Adenoviral Vector Construction

The non-replicative adenovirus Ad.CAG-MyoD was engineered using an adenovirus type 5 and the murine MyoD gene (Gene ID 17927, NCBI) using the Sander method [21]. The same technique was used for the production of the EGFP control virus. Cells were infected with an adenovirus expressing MyoD under the ubiquitous CMV early enhancer/chicken β-actin promoter [37] (Ad.CAG-MyoD). Briefly, we excised the MyoD expression unit containing murine MyoD cDNA under the control of the CAG promoter from pCAGGS-MyoD. Murine MyoD cDNA is described in accession no. NM_010866.2. The CAGGS-MyoD unit was inserted into the SwaI site of the pAdexIw cosmid that contained the genome of adenovirus type 5 without the E1 and E3 regions. The cosmid was co-transfected with the EcoT221-digested adenovirus DNA-terminal protein complex into 293 cells by calcium phosphate co-precipitation. The recombinant adenovirus vector, Ad.CAGMyoD, was isolated, amplified and purified by double CsCl gradient centrifugation [21]. The titer of Ad.CAGMyoD determined by the end-point cytopathic assay was $1\times10^9$ PFU/ml.

The control vector, Ad.CAG.EGFP, which contained the EGFP cDNA under the control of the CAG promoter, was prepared in the same manner as Ad.CAG.MyoD and the titer was $1\times10^9$ PFU/ml. The final preparations were stored at −80° C.

Viral Production

The virus was produced in the 293 cell line. The cells were plated at approximately 70% confluence on attachment Petri dishes in DMEM 10% FBS+1% Penicilin/Streptavidine (P/S). The following day, the cells were infected with the Ad.CAG-MyoD at a MOI of 3 and the cells were left in culture for a period of 48 hours. After this period, the cells were gently detached from the Petri dishes by doing up and down with the culture media. The medium was recuperated and three freeze and thaw cycles were performed to lyse the cells. The virus was then purified from the medium using the $CaCl_2$ technique.

Colony Infection

Colonies that did not reach confluence, approximately 3 to 4 days after passaging the cells, were infected with different viral titers, from 1E5 to 1E8 viral particles, for a period of 6 hours in serum-free alpha-MEM (Minimum Eagle medium). After this period, the cells were washed twice with PBS (Phosphate buffered saline) and put back in culture medium, composed of alpha-MEM, 20% FBS, 1% NEAA, 1% L-Glu, 1% P/S and 10 μM mono-thioglycerol. The cells were grown for a period of five more days and fixed with 95% ethanol for immunocytochemistry.

Single Cell Infection hESC colonies that reached confluence were first treated with 10 μM of ROCK (Rho kinase) inhibitor for a period of 1 hour. The colonies were then dissociated using a traditional solution of 0.5% Trypsin. Cells were seeded on a petri dish coated with MATRIGEL at 12500 cells/cm² and put back in culture in the MTESR1 medium containing 10 μM ROCK inhibitor for a period of 24 hours. The cells were then infected for 6 hours at different MOIs in alpha-MEM media containing 10 μM of ROCK inhibitor. Finally, the cells were washed twice with PBS and put back in culture in medium MTESR1 medium supplemented with 10 μM ROCK inhibitor.

MCM1 Culture Medium:

The composition of the MCM1 culture medium is as follows:

| | mg/L |
|---|---|
| AMINO ACID | |
| L-Alanine | 2.67 |
| L-Arginine•HCl | 210.67 |
| L-Asparagine•H2O | 15.01 |
| L-Aspartic Acid | 13.31 |
| L-Cysteine•HCl•H2O | 35.13 |
| L-Glutamic Acid | 4.41 |
| L-Glutamine | 1461.5 |
| Glycine | 2.25 |
| L-Histidine•HCl•H2O | 41.93 |
| L-Isoleucine | 65.58 |
| L-Leucine | 131.17 |
| L-Lysine•HCL | 181.65 |
| L-Methionine | 29.84 |
| L-Phenylalaline | 33.04 |
| L-Proline | 11.51 |
| L-Serine | 31.53 |
| L-Threonine | 35.73 |
| LTryptophan | 4.08 |
| L-Tyrosine | 18.12 |
| D-Valine | 117.15 |
| VITAMINS | |
| d-Biotin | 0.00733 |
| Folinic Acid (Ca salt)•5H2O | 0.602 |
| DL-alpha-Lipoic Acid | 0.002063 |
| Niacinamide | 6.11 |
| D-Pantothenic Acid (hemi-Ca salt) | 23.82 |
| Pyridoxine•HCL | 2.056 |
| Riboflavin | 0.003764 |
| Thiamin•HCL | 3.373 |
| Vitamin B12 | 0.01355 |
| OTHER ORGANIC COMPONENTS | |
| Adenine | 0.1351 |
| Choline Chloride | 13.96 |
| D-Glucose | 1000 |
| myo-Inositol | 18.016 |
| Putrescine•2HCL | 0.0001611 |
| Sodium Pyruvate | 110.04 |
| Thymidine | 0.02422 |
| BULK INORGANIC SALTS | |
| $CaCl_2•2H_2O$ | 235.23 |
| KCl | 298.2 |
| $MgSO_4•7H_2O$ | 246.38 |
| NaCl | 6430 |
| $Na_2HPO_4•7H_2O$ | 134.04 |
| TRACE ELEMENTS | |
| $CuSO_4•5H_2O$ | 0.002496 |
| $FeSO_4•7H_2O$ | 0.834 |
| $H_2SeO_3$ | 0.00387 |
| $MnSO_4•5H_2O$ | 0.000241 |
| $Na_2SiO_3•9H_2O$ | 2.842 |
| $(NH_4)_6Mo_7O_{24}•4H_2O$ | 0.00371 |
| $NH_4VO_3$ | 0.000585 |
| $NiCl_2•6H_2O$ | 0.0000713 |
| $ZnSO_4•7H_2O$ | 0.08625 |
| BUFFERS, INDICATORS AND MISCELLENOUS | |
| Phenol Red (Na salt) | 1.242 |
| $NaHCO_3$ | 1176 |
| Serum | 0.5-30% |
| bFGF | 0.1 |
| BSA | 500 |

-continued

| | mg/L |
|---|---|
| dexamethasone | 2 |
| insulin | 5 |

Of course it will be apparent to the skilled person that modifications to the above concentrations can be made or that some constituents can be omitted. For example, pH indicators can be omitted and amino acids, vitamins, salts, trace elements, BSA, dexamethasome, bFGF and insulin concentrations can be varied (e.g., +/−10% concentration variation) without substantially affecting the function and effects of the myogenic culture medium described above.

Myotube Formation

Myogenic cell differentiation was induced by growing them to 70% confluence and reducing the serum concentration, i.e., the medium A was changed for D-MEM containing 2% FBS and 1% P/S. The cells were then cultured for 7 days before fixation with ethanol 95%.

RNA Isolation and RT-PCR

RNA was isolated using TRIZOL (Invitrogen) and its purity was determined by spectrophotometry. A DNAse 1 (Roche) treatment was then made for a period of 1 hour at 37° C. The enzyme was then inactivated with 25 μM EDTA and by heating at 42° C. for 15 minutes. The RNA was then transcribed in cDNA using the OMNISCRIPT RT kit (Qiagen). The cDNA was then amplified using TAQ polymerase (Qiagen). The primer sequences, the temperature, the cycle number and the size of the amplicons are found in Table 1.

were incubated with CD73-APC and CD56-PE antibodies at the same time using the same protocol. For SSEA4 labeling the cells were washed, then incubated with an anti-mouse IgG coupled with FITC (Invitrogen) for 45 minutes at a dilution of 1:300 in FACS buffer. The cells were then analyzed by FACS.

Immunocytochemistry

Cells were first fixed with a 95% ETOH solution for 15 minutes. After washing, non-specific binding of antibodies was blocked by a 1 hour incubation in PBS, −10% FBS. The first antibody was then incubated in PBS 1% FBS as recommended by the manufacturer (i.e. 1:75 for desmin (Dako, d33) and 1:50 for MCH (Mouse anti-MyHC mAb MF20, DSHB, Iowa city, IA)). The second antibody coupled either with ALEXA FLUOR 488 or ALEXA FLUOR 546 (Invitrogen) was incubated at a dilution of 1:250 in PBS for 45 minutes. The cells were finally stained with DAPI diluted at 1:10000 for 3 minutes. For the analysis (n=3), the cells of three random fields were manually counted under a microscope. All values are expressed as means±standards error of the mean (SEM).

Immunoperoxidase

Cells were fixed in 100% methanol for MyoD staining. Nonspecific reactions were blocked with 1% bovine serum albumin (BSA). Cells were then incubated overnight at 4° C. with the primary antibodies at the dilutions recommended by the manufacturer (Santa Cruz, 1/200). After 3 washes, the cells were incubated with the secondary antibodies for 45 minutes at room temperature. Biotin-conjugated secondary antibodies (1:150) were used for immunoperoxydase staining. These antibodies were revealed with a streptavidin-coupled HRP-signal amplification kit followed by DAB detection.

TABLE 1

Primer sequences, PCR conditions and amplicon sizes for RT-PCR analysis.

| Gene name | Orientation | Number cycle | Ann. Temp. | Size | SEQ ID NO: | Sequence |
|---|---|---|---|---|---|---|
| Oct4 | antisense | 35 | 58 | 422 pb | 4 | ATTTGCCAAGCTCCTGAAGCAG |
| | sense | | | | 5 | TTGATCGCTTGCCCTTCTGG |
| Nanog | antisense | 35 | 58 | 378 pb | 6 | AGTGTGGATCCAGCTTGTCCC |
| | sense | | | | 7 | TTCTTGCATCTGCTGGAGGC |
| REX-1 | antisense | 35 | 58 | 255 pb | 8 | AGTCAAGCCAAGACCTGCAGG |
| | sense | | | | 9 | GGGAGCTTGCTTCGAAAACC |
| Pax7 | antisense | 10 + 25 | 68, 64 | 389 pb | 10 | CAAGATTCTTTGCCGCTACC |
| | sense | | | | 11 | TTCAGTGGGAGGTCAGGTTC |
| Myf5 | antisense | 10 + 25 | 68, 64 | 320 pb | 12 | GTTAAGCATTGCAACAAGCTACCC |
| | sense | | | | 13 | CCAGGCTTATCTATCATGTGCTATG |
| MyoD | antisense | 35 | 63 | 430 pb | 14 | CGATATACCAGGTGCTCTGAGGG |
| | sense | | | | 15 | GGGTGGGTTACGGTTACACCTGC |
| Myogenin | antisense | 35 | 58 | 438 pb | 16 | TAAGGTGTGTAAGGGAAGTCG |
| | sense | | | | 17 | CCACAGACACATCTTCCACTGT |
| MHC | antisense | 36 | 63 | 850 pb | 18 | CTGCTGAAGGAGAGGGAGCT |
| | sense | | | | 19 | TGATTAGCTGGTCACACCTT |
| GAPDH | antisense | 30 | 56 | 342 pb | 20 | CCCCTTCATTGACCTCAACTACA |
| | sense | | | | 21 | TTGCTGATGATCTTGAGGCTGT |

FACS Analysis

Cells were detached from the dish using 0.05% trypsin, pelleted and washed with PBS. The cells were incubated with the appropriate antibody against SSEA4 antibody (Abcam, MC813, CD-73 or CD-56-PE) at a dilution of 1:65 in FACS buffer (PBS, 5% FBS) for one hour. For double labeling, cells Immunohistochemistry Tibialis anterior (TA) muscles of Rag/mdx mice were removed 1 month after myoblast transplantation. Frozen muscle cross-sections were blocked in PBS with 10% FBS and 2% BSA for 1 hour and then incubated overnight at 4° C. with the mouse mAb for human dystrophin (MANDYS104, a generous gift from Dr. Glen Morris, MRIC Biochemistry Group, Wrexham, UK) diluted 1:10. Finally, muscle sections were incubated 1 hour with a goat anti-mouse ALEXA FLUOR 488 (diluted 1:250). Cross-sections were washed with PBS before and after incubation with both antibodies. A mouse monoclonal anti-β chain of spectrin (NCLSPEC1) antibody was used diluted 1:100 to detect spectrin. Muscle cross-sections were blocked in PBS with 10% FBS, 2% BSA 1 hour and then incubated overnight at 4° C. with the primary antibody. Muscle sections were incubated 1 hour with a goat anti-mouse ALEXA FLUOR 546.

Cell Proliferation Assay

The cell proliferation assay was performed using a CYQUANT cell proliferation assay kit, which measures the nucleic acid content in the test samples. The cells were harvested after various treatment times and stored at −80° C. until the analysis. The frozen micro-plates were then thawed at room temperature and the CYQUANT GR dye/cell lysis buffer was added. After incubating for 5 minutes, the fluorescence was measured (excitation/emission: 495/520 nm) using a micro-plate reader.

Cell Transplantation

Primary normal human myoblasts were obtained and proliferated as described previously [38, 39]. The day of transplantation, cells were trypsinized and washed first in DMEM containing 10% FBS and then in HBSS, before being resuspended in 20 µl of HBSS. The left and right TAs were surgically exposed and 0.5 million cells were coinjected with cardiotoxin (100 µg/ml) at 10 to 15 sites throughout each TA muscle as previously described by our group [40]. Rag/mdx mice were transplanted either with myoblasts, hESCs, MB1-hESCs, MB1-MyoD-hESCs, hiPSCs, MB1-hiPSCs or MB1-MyoD-hIPSCs. Another negative control mouse group was injected in one TA only with HBSS. The fusion of human cells with the mouse muscle fibers was assessed 1 month later by detecting the presence of human spectrin or human dystrophin.

Karyotyping

Dividing cells were arrested in metaphase with colcemid overnight, hypotonically shocked with KCl, and fixed with methanol/acetic acid (3/1; vol/vol). Chromosomes were identified using RHG-banding technique. At least 30 mitoses were examined for each karyotype.

Statistical Analysis

All data are expressed as means±SEM and are representative of at least three separate experiments. The statistical significance of the difference between groups was determined by a Student's t-test. A value of $P<0.05$ was considered significant.

Example 2

Growth Characteristics of Undifferentiated hESCs

After a period of mechanical and enzymatic passages, the differentiated cells of the hESC H9 cell line were eliminated and the culture showed characteristics of undifferentiated hESCs. The colonies showed typical characteristics of hESCs grown on MATRIGEL such as a well definite boundary, a high nucleus/cytoplasm ratio and growth in a single layer (FIG. 1A). A FACS analysis for the SSEA4 marker, which is specific to the embryonic stage, confirmed the undifferentiated state of our H9 culture with almost 95.3% of the cells staining positive for this specific antigen (FIG. 1C). Results have been confirmed by immunohistochemistry (FIGS. 1B (Hoechst staining) and D (SSEA4 staining)). At this stage, in contrast to myoblasts (FIG. 1F), the myogenic marker the myogenic marker, Myosin Heavy chain (MHC) was not expressed in hESCs(FIG. 1E). These cells were used for further differentiation experiments.

Example 3

Growth in Colonies Block the Myogenic Pathway

Figure 2:
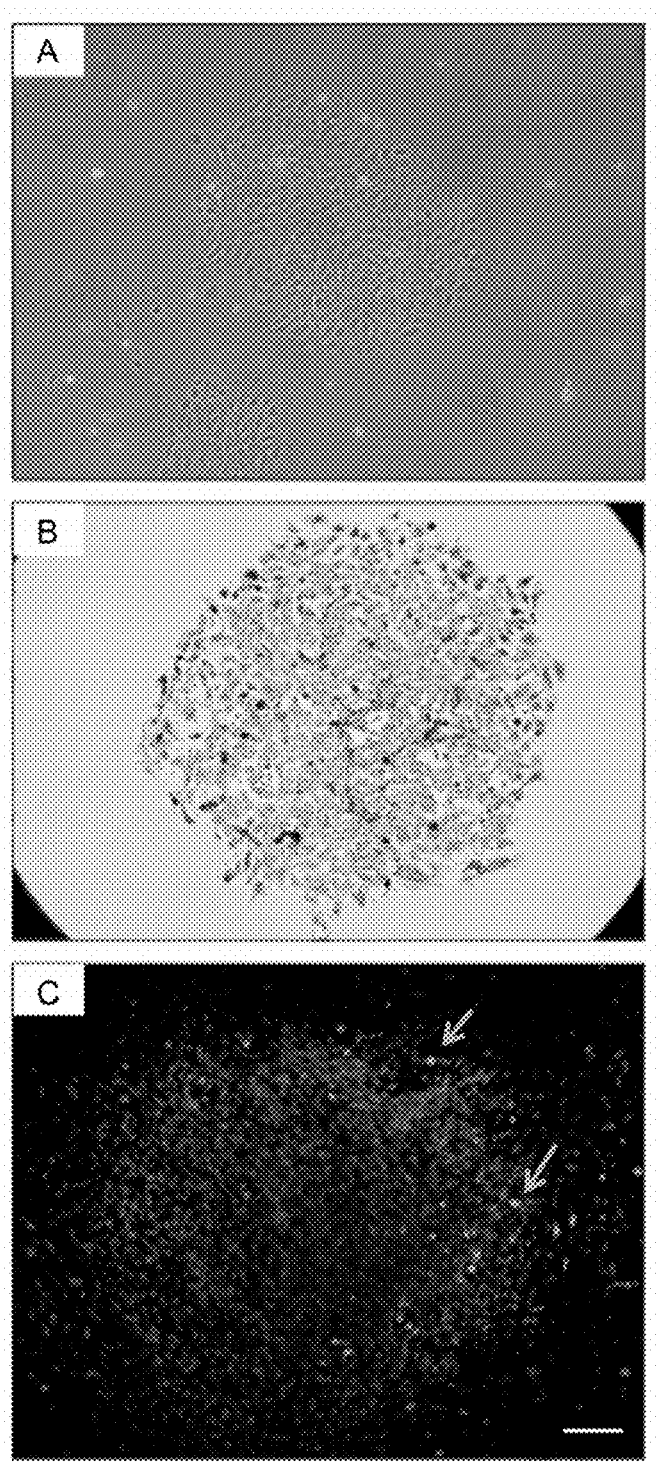
FIG. 2 shows colony infection.

Initially, hESCs grown in colonies were infected with an adenovirus containing a mouse MyoD gene under a CMV early enhancer/chiken β-actin promotor (ad.CAG-MyoD). The exact MOI could not be established, thus, predetermined/fixed concentrations of Ad.CAG-MyoD and of a control virusfrom 1E5 to 1E8 viral particles per well of a 24 wells plate, were used for infection. An adenovirus (Ad.CAG-GFP) coding for GFP under the same promoter was used as a negative control. As soon as 24 hours after the infection, evidences of differentiation were observed regardless of the virus and of the viral concentration. This could be due to change in the culture medium at the time of viral infection. Colonies started to lose their definite boundary and the cytoplasm of cells expanded (FIG. 2A). However, immunostaining performed five days post-infection revealed that only a few cells of the colonies were infected by the adenovirus (Ad.CAG-MyoD) and expressed the MyoD transgene (FIG. 2B). This poor infection rate resulted in a inefficient myogenic conversion of the hESCs based on the expression of desmin, another myogenic marker. In fact, the best results were obtained with the highest viral concentration and the conversion rate to myogenic cells was below 1%, based on desmin expression (FIG. 2C). However, desmin positive cells were only observed when the cells were infected with the Ad.CAG-MyoD and no positive cells were observed in the negative control.

Example 4

Single Cell Infection Improves Infection and Differentiation

Figure 3:
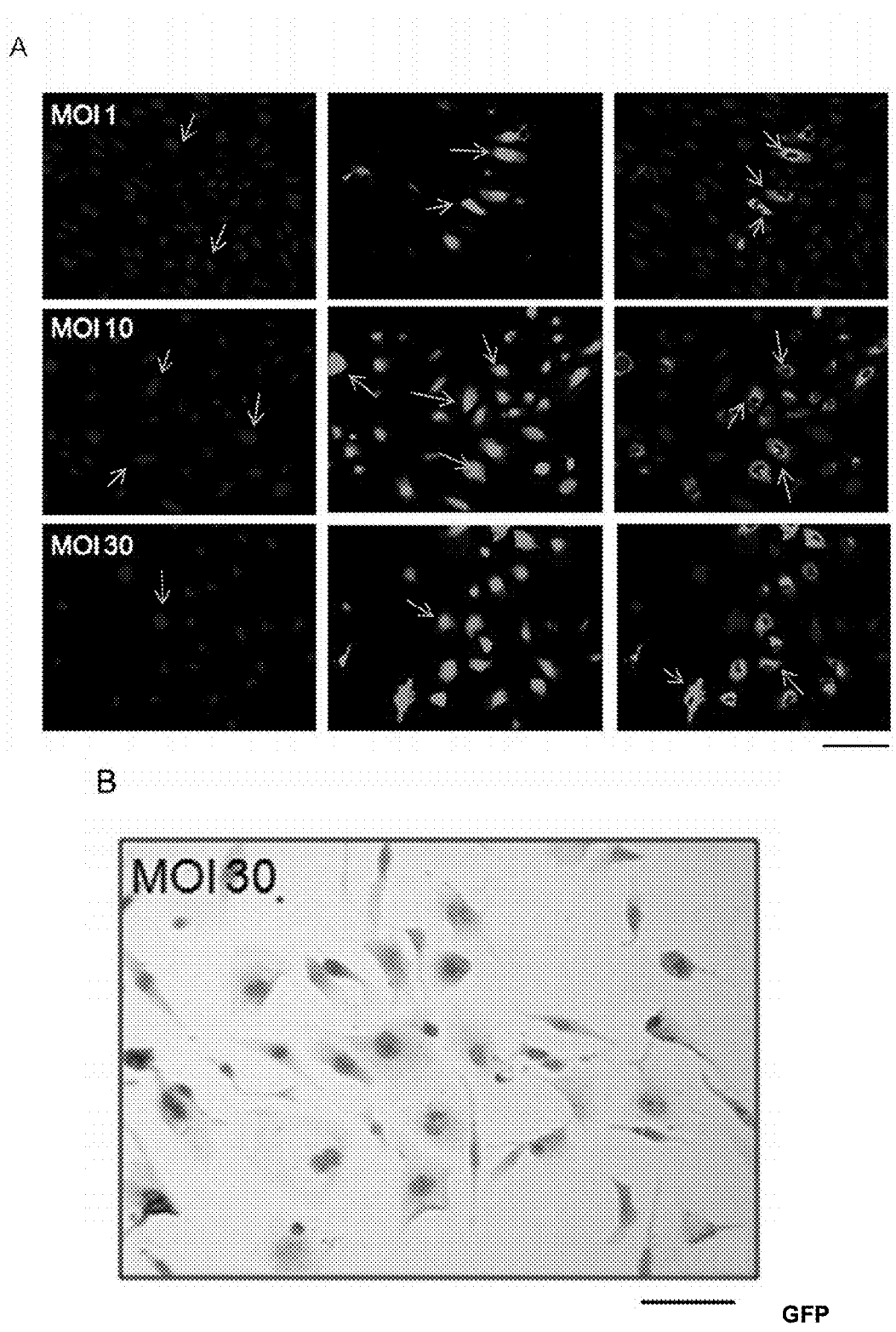
FIG. 3 shows infection of isolated hESCs with Ad.CAG-MyoD.
Figure 3:
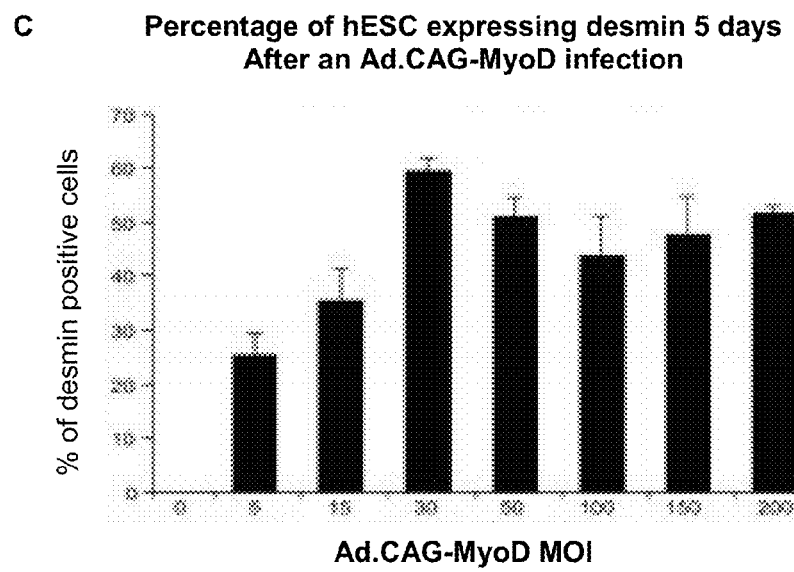
Figure 3:
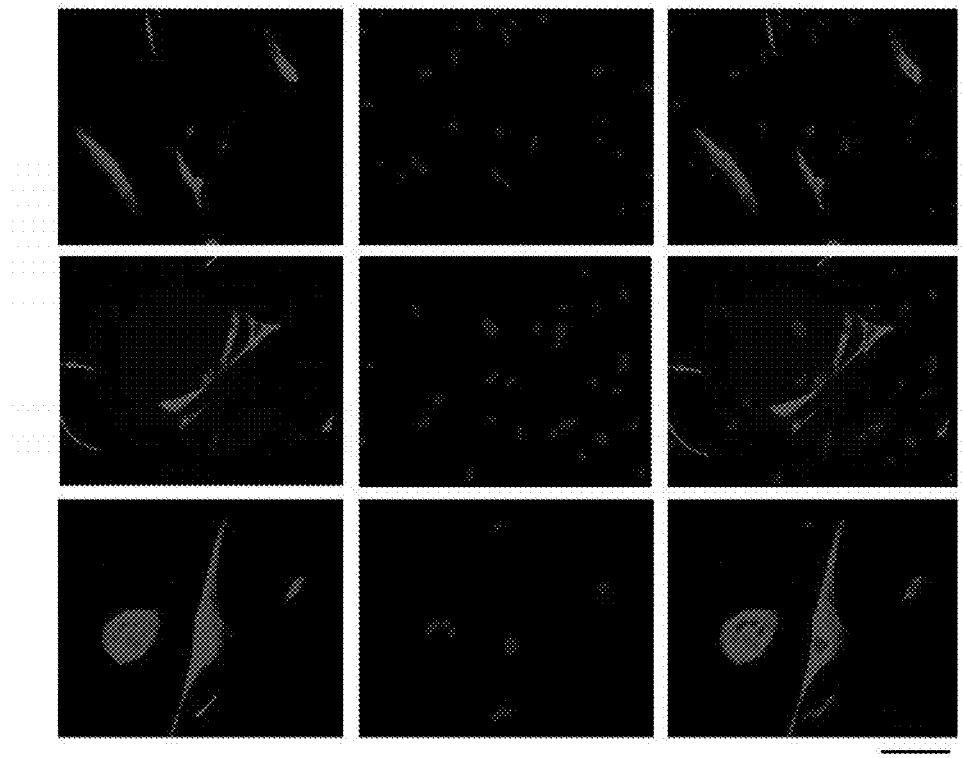

Since the results presented in Example 2 demonstrated that MyoD transgene expression induced myogenic differentiation of some hESCs but that colonies limited the infection rate, we tried to infect hESCs grown as single cells with different MOI. This protocol modification also had the advantage to improve the infection reproducibility since we were able to count the number of cells plated per wells. For this, we modified the culture conditions before infection with the AD.CAG.MyoD by adding a ROCK-inhibitor to prevent cell death by anoïkis (FIGS. 3, and 9a and b), however cell death remained elevated. This cell death was due to the fact that hESCs had less cell/cell contacts. Thus, despite the presence of the drug, cell death was still elevated, although at a lesser extent. The cells were then infected at different MOIs using Ad.CAG-MyoD and the GFP control virus (Ad.CAG-GFP). Following infection, changes in the morphology of the infected cells were observed. The cells adopted a shape more similar to myogenic cells with a long cytoplasm. Five days post-infection, the cells were fixed and stained to determine the percentage of cells expressing the transgene. A MOI-dependant expression of the transgene was observed (FIG. 3A). Positive cells were observed at a MOI as low as 1 and nearly 100% of the hESC infected with the Ad.CAG-MyoD stained positive at a MOI of 30 (FIG. 3B). Confluency (cell growth) was reduced in cells infected with MyoD compared to the control. To verify whether the infected cells undergo myogenesis, a desmin staining was performed. A MOI of 5 was found sufficient to induce myogenesis of 26±4% of the cells. A correlation between the MOI and the amount of desmin-positive cells was observed for MOIs between 0 and 30 (FIGS. 3C, E). More precisely, MOI of 5, 15 and 30 allowed the myogenic differentiation of 26±4%, 36±6% and 60±2% of cells respectively. When the cells were infected with a MOI above 30, a stabilization of the percentage of hESCs which underwent myogenesis was observed due to a diminution of proliferation and to an increase in mortality. For this reason, all the experiments realized after this point were done using a MOI of 30 to induce the myogenesis of the hESCs.

The karyotype of hESC cells and infected cells has also been investigated. Except for a decrease in mytotic indices (MyoD is known to decrease cell proliferation), cells did not show any karyotype abnormalities.

The results demonstrate that adenovirus is a good vector to infect hESCs grown as single cells since positive cells for the transgene MyoD or GFP were detected at a MOI of 1 and that almost 100% of the cells stained positive at a MOI of 30 or higher. The expression of MyoD in hESCs also correlated with a diminution of proliferation of the hESCs. This phenomenon can be attributed to the myogenic transcription factor which is known to inhibit proliferation [20]. Based on the desmin expression, a myogenic specific protein, the force expression of MyoD in hESCs is sufficient to induce their myogenesis in a dose-dependent manner until a critical point where the differentiation rate reached a plateau. Compared to earlier, published techniques to differentiate hESCs in muscle cells [6, 22, 23], it is the first time that such a level of efficiency is obtained.

Example 5

In Vitro Differentiation Potential of hESCs

To determine whether skeletal muscle cells derived from hESCs were able to form myotubes, infected cells were grown under low serum conditions (2% horse serum). The medium was changed 5 days post-infection. Under low serum conditions, a significant increase in cell mortality was observed compared to the positive control, a human myoblast primary culture. Morphological change of infected cells was observed, i.e., they became more elongated and formed extensions like myoblasts under the same conditions. To determine if the infected cells underwent terminal differentiation under these conditions, immunocytochemistry against the myosin heavy-chain (MHC), a myotube specific protein, was performed 4 days after the medium was changed. 20±3 of the MyoD infected hESCs expressed the MHC under low serum conditions. Myotubes containing only from 2 to 5 nuclei were observed (FIG. 3E) and the majority of the MHC positive cells grew as single cells. These results indicated that the MyoD infected hESCs do not only undergo myogenesis but that they are functional and can participate to the formation of myotubes. However, the fusion potential of the MyoD infected cells was not as high as that of primary culture of myoblasts, which formed myotubes containing more than 10 nuclei. This difference between the two cell lineages may be attributed to the low confluence of the infected cells, which is caused by the increased mortality of this cell population in the low serum medium. Another limiting factor is the presence of a heterogeneous population in which almost 40% of the cells are not myogenic lineage and do not have a fusion potential.

Example 6

Figure 4:
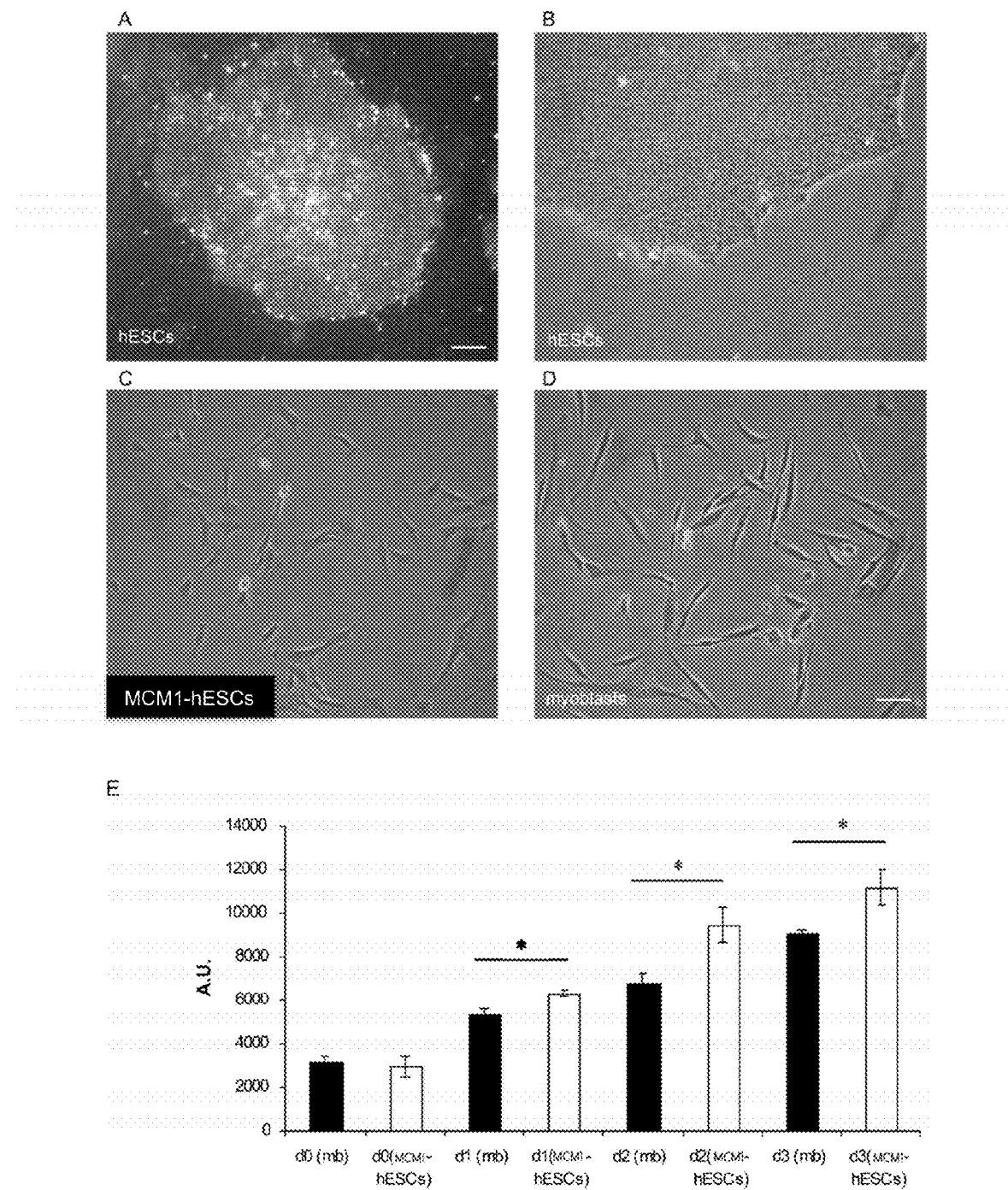
FIG. 4 shows changes in the morphology of hESCs after culture in MCM-1 medium. The morphology of hESCs changed following their culture in a myogenic culture medium (MCM1) for one passage (FIG. 4C), the MCM1-hESCs had a flat spindle morphology more similar to myogenic cells (FIG. 4D) than to embryonic stem cells (FIG. 4A, B). The fluorescence intensity of the CYQUANT GR dye was measured at different times (0, 1, 2, 3 days (d0, d1, d2, and d3)) to evaluate the proliferation in MCM1 medium (FIG. 4E). An increased proliferation of MCM1-hESCs compared to myoblasts was observed at all time intervals. The * indicates statistically different results, n+3, p<0.05. Scale bars are respectively 300 µm in A, 60 µm in B, C and D.
Figure 6A:
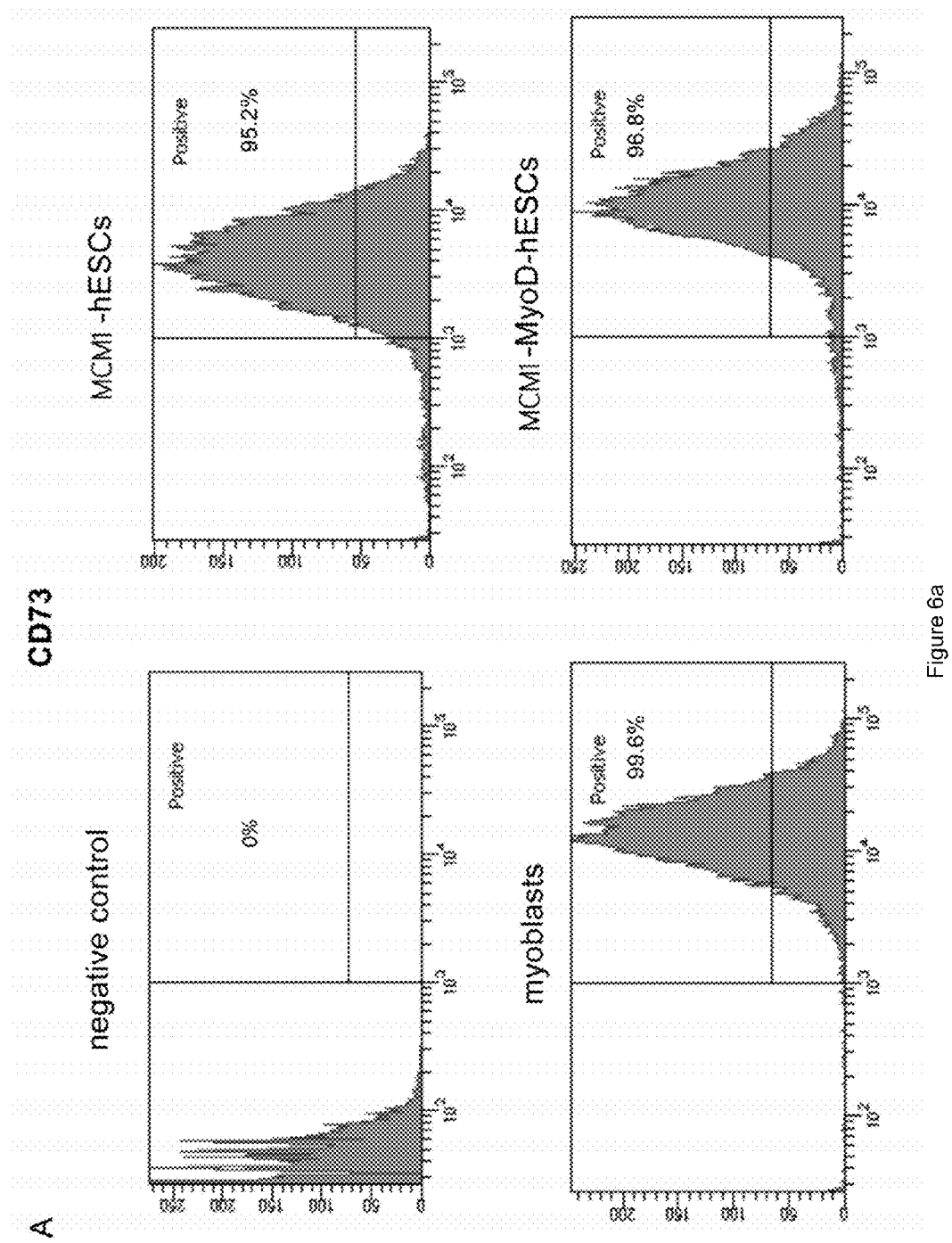
FIG. 6A: Culture of hESCs in MCM1 culture medium induced their differentiation into mesenchymal-like stem cells expressing CD73.
Figure 7:
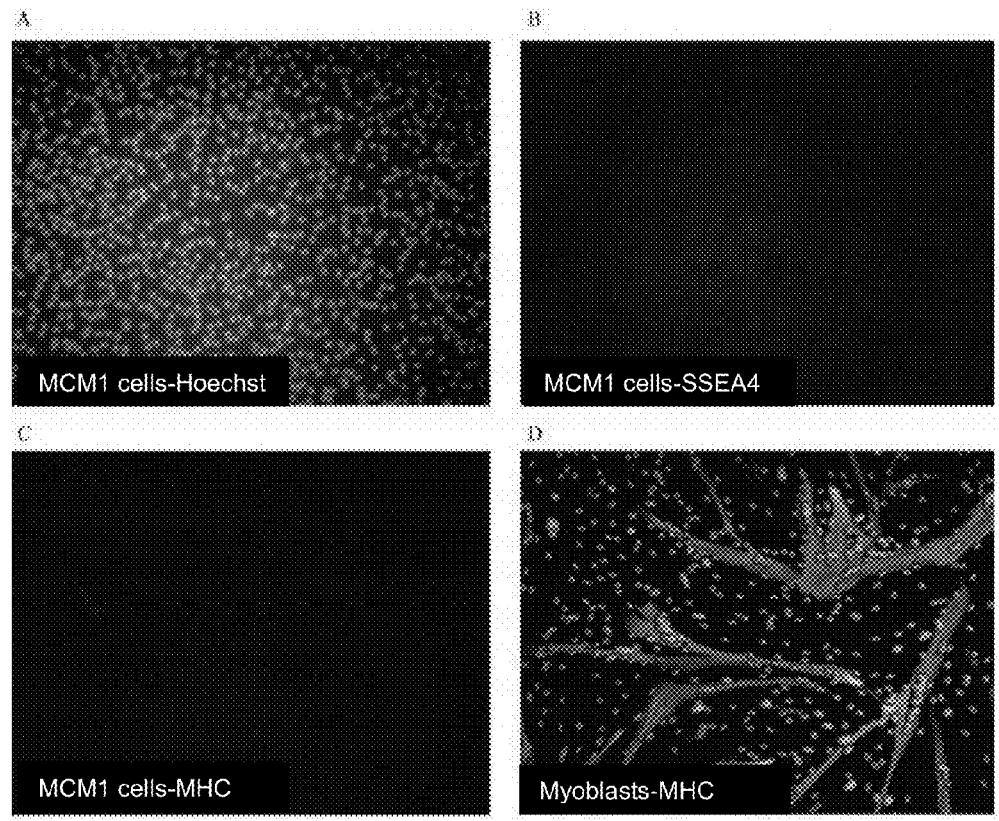
FIG. 7 shows immunocytochemistry of the embryonic marker SSEA4 and myogenic marker MHC on hESCs grown in MCM1 culture medium.

Culture in Myogenic Medium MCM1 Results in Determination of Cells to Mesenchymal Lineage First, the present inventors developed a simple culture system to induce mesenchymal-like differentiation of ESCs based on selective culture conditions. This second protocol was based on growth of hESCs in a myogenic culture medium (MCM1) currently used to proliferate human myoblasts for clinical transplantations. Undifferentiated hESCs were thus transferred from their MTESR1 medium to the MCM1 medium containing 15% FBS (on MATRIGEL for the first 5 days in culture). Following 2 passages in culture, changes in the morphology of the cells were observed (FIG. 4C). The cells exhibited a flat spindle-like morphology more similar to myogenic cells (FIG. 4D) than to ESCs (FIG. 4 A-B). Immunocytochemistry confirmed the loss of embryonic marker SSEA4 (FIG. 7B) expression but always without myogenic marker like MHC after 2 weeks in differentiation medium (FIG. 7C). So far we have demonstrated that the proliferation of hESCs in the MCM1 culture medium induced a transformation of these cells into mesenchymal like stem cells since they expressed CD73 (100%) (FIG. 6A).

Example 7

Gene Expression Following MyoD Infection

Figure 5:
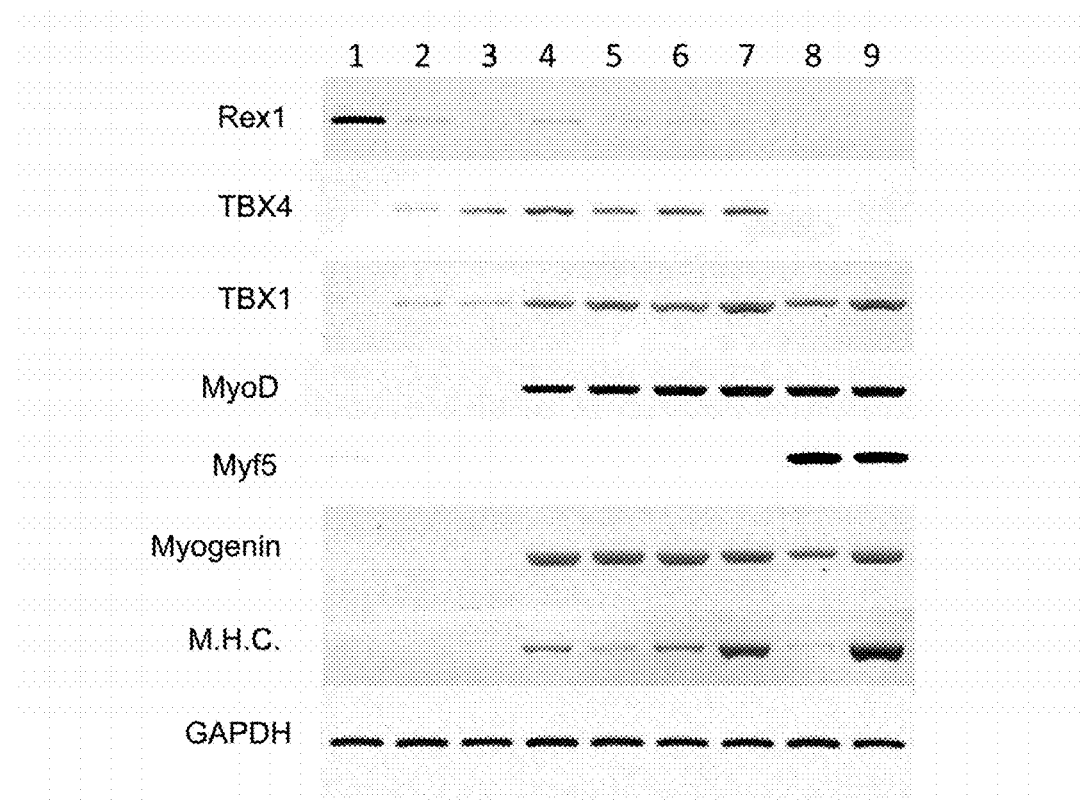
FIG. 5 shows RNA expression of various factors following culture in MCM1 medium and infection with MyoD. Infection of MCM1-hESCs with the Ad.CAG-MyoD induced the expression of diverse myogenic genes. Three days following infection, MCM1-MoyD-hESCs expressed early and late myogenic genes (MyoD, myogenin, MHC) except the transcription factor Myf5. Compared to the undifferentiated hESCs, a diminution of embryonic gene expression (REX1) was observed in the MCM1 medium. RT-PCR analysis showed a time-dependent, sequential differentiation of hESCs into myogenic cells with a mesenchymal step (TBX1 and TBX4). 1. hESC grown in MTESR1; 2. hESCs grown in MCM1; 3. hESCs grown in MCM1, first passage without MATRIGEL; 4. hESCs grown in MCM1 and infected with Ad.CAG-MyoD, day 3 in proliferation; 5. hESCs grown in MCM1 and infected with Ad.CAG-MyoD, day 1 in differentiation; −6. hESCs grown in MCM1 and infected with Ad.CAG-MyoD, day 3 in differentiation; 7. hESCs grown in MCM1 and infected with Ad.CAG-MyoD, day 5 in differentiation; 8. Myoblasts in proliferation; 9. Myoblasts in differentiation.

In order to induce their myogenic differentiation, the MCM1-hESCs were infected with an adenovirus coding for myoD (Ad.CAG-MyoD). RT-PCR was used to analyse the changes in gene expression at various steps of the differentiation protocol: 1) Following the transfer of hESCs from the MTESR1 to the MCM1 medium containing 15% FBS (MCM1-hESCs), 2) following their subsequent infection with the Ad.CAG-MyoD (MCM1-MyoD-hESCs); and 3) Following their transfer from the proliferating conditions to a differentiation medium (DMEM with 2% FBS) (FIG. 5). RNA was thus collected before and after the MCM1 transfer, 3 days after their infections and at days 1, 3 and 5 after their transfer in the differentiation medium. As a negative control, the RNA of hESCs infected with the Ad.CAG-GFP was collected after 10 days. The RT-PCR analysis indicated that a MyoD infection was sufficient to induce the expression of several myogenic genes. The undifferentiated specific gene Rex-1 (as well as Nanog and Oct4, data not shown) considerably decreased from hESCs to MCM1-hESCs but was still expressed at a very low level following the MyoD infection (MCM1-MyoD-hESCs). However, the expression of these genes was diminished compare to GFP control meaning that the MyoD expression led to a better differentiation of the hESCs.

As soon as hESCs were transferred in MCM1, we also observed the expression of paraxial mesoderm, TBX4 and TBX1, which regulates Myf5 and MyoD. The expression of these markers was further increased after MyoD infection. TBX4 is important for the development of the limb buds. The pre-myogenic specification marker TBX1 is expressed in the pre-myogenic mesoderm of the first and 2nd branchial arch before the onset of MRF expression. The RT-PCR analysis also indicated that the infection with Ad.CAG-MyoD coding for a mouse MyoD gene was sufficient to induce the expression of several human myogenic genes. The MCM1-MyoD-hESCs expressed the endogenous, i.e., human, transcription factor MyoD as confirmed by RT-PCR using primers specific for the human mRNA. In addition, we observed the presence of human myogenin and of MHC, which are late myoblast markers that are expressed during the terminal differentiation into myotubes [16]. Expression of these myogenic genes in MB1-MyoD-hESCs can be directly linked to the MyoD expression since these genes were not expressed in the hESCs control and in the MCM1-hESCs. However, compared to the real human myoblasts, the MCM1-MyoD-hESCs did not express the transcription factor Myf5.

During embryogenesis, Myf5 and MyoD play different roles and are responsible for the formation of two different muscle lineages [24, 25]. However, a compensation mechanism allow only one of these transcription factors to be required for skeletal myogenesis in mutant mice [26] and they can both participate to the activation of quiescent satellites cells [27]. Furthermore, MyoD is expressed upstream of Myf5 [28] and its overexpression has been shown to inhibit the expression of Myf5 [29]. Similar results have been also observed with human adipose-derived stem cells infected with a MyoD lentivirus [13].

Also, at day 5 post infection, we observed the expression of Pax7, which is a marker of satellite cells (data not shown) [15]. Ten days after the infection with Ad.CAG-MyoD, an upregulation of the primitive skeletal muscle marker Pax 7, a diminution of MyoD and of myogenin and the absence of MHC were observed (data not shown).

Furthermore, we observed that the MyoD transgene can upregulate the expression of the human MyoD gene. This result indicated that the murine transcription factor can regulate the endogenous gene the same way it is occurring during skeletal muscle development [34].

Taken together, these results illustrate the developmental progression of stem cells toward myogenic lineage through a transient mesodermal stage.

Example 8

Myogenic Conversion of Cells Grown in MCM1 Medium

Figure 6B:
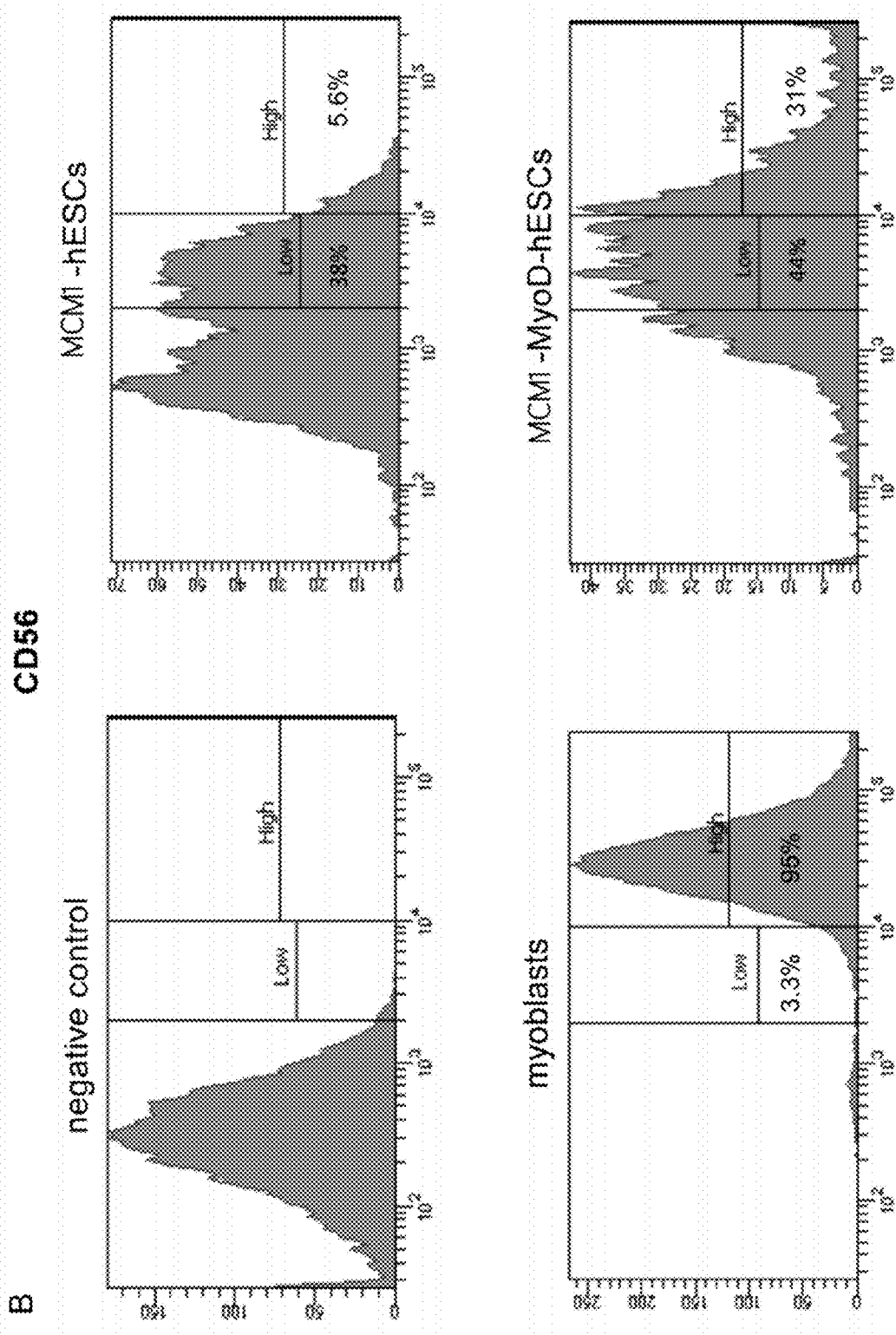
FIG. 6B: However, in the MCM1 medium, less than 6% of these CD73 cells also expressed CD56. Infection of these CD73 cells with the Ad.CAG-MyoD construct induced their conversion in cells called MCM1-MyoD-hESCs expressing high CD56 level (31%). Negative control: fibroblasts. Positive control: myoblasts.
Figure 8:
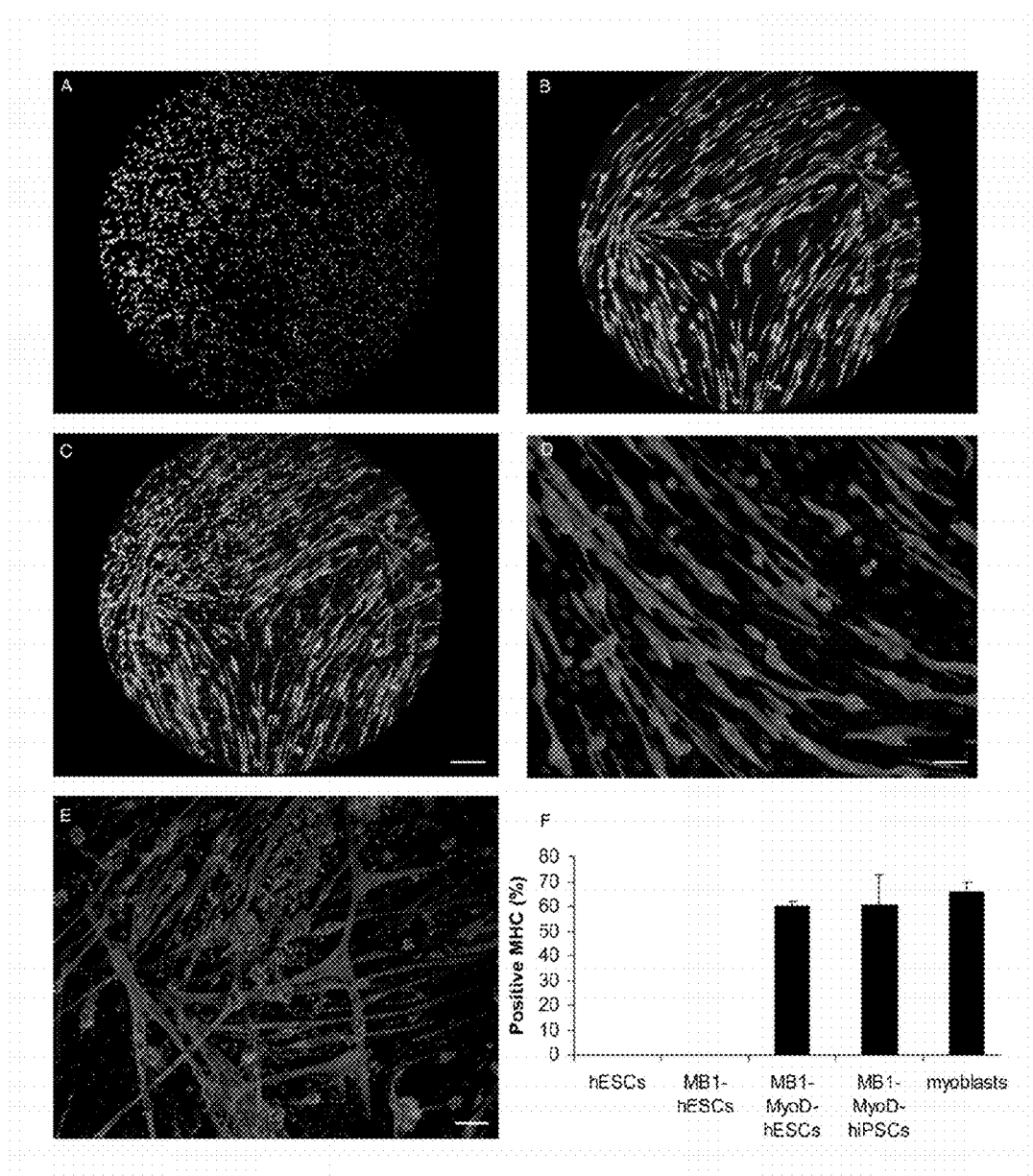
FIG. 8 shows the in vitro terminal differentiation of MCM1-MyoD-hESCs and dystrophic MCM1-MyoD-hiPSCs. The MHC immunochemistry in red showed that when cultured in MCM1 medium and infected with the Ad.CAG-MyoD construct, the MCM1-MyoD-hESCs (A-D) and the dystrophic MCM1-MyoD-hiPSCs (E) acquired skeletal muscle cell properties and fused to form multinucleated myotubes when cultured under low serum condition (2% serum). The fusion potential was equal to that of myoblast primary culture. 60% of the cells expressed MHCs and most of the cells were differentiated in myotubes, some of them containing up to 20 nuclei. There was no significant difference between MCM1-MyoD-hESCs, MCM1-MyoD-hiPSCs and myoblasts (F). The scale bar of 400 µm applies to A and B. The scale bar is 30 µm in D and 150 µm in E.
Figure 9:
FIG. 9 shows a cytogenetic analysis of hESCs. The karyotype of cells was investigated by cytogenetic. (A) hESCs in single cells. (B) hESCs in single cells infected with Ad.CAG-MyoD. (C) MCM1-hESCs. (D) MCM1-MyoD-hESCs. (E) MCM1-hiPSCs. (F) MCM1-MyoD-hiPSCs. Except a decrease in mitotic index after infection with Ad.CAG-MyoD, cells did not show any karyotype abnormalities.

In the previous examples it was shown by RT-PCR that MCM1-hESCs expressed the mesodermal genes TBX1 and TBX4. To verify a potential mesenchymal-like differentiation, the expression of the surface antigen CD73 was first verified by FACS at around day 3 of culture in MCM1 medium (FIG. 6A). CD73+ is expressed by mesenchymal multipotent precursors, which can be induced to differentiate in bone, cartilage, fat and skeletal muscle cells [6]. Before infection with Ad.CAG.MyoD, less than 6% of the CD73 positive MCM1-hESCs expressed a high level of CD56, a marker of myoblasts (FIG. 6B). However, the infection of MCM1-hESCs CD73 positive cells with the Ad.CAG. MyoD adenovirus induced their transformation into cells expressing CD56 (31% of MCM1-MyoD-hESCs were CD56high and an additional 44% were CD56low). With adult mesenchymal stem cell (hMADS), results obtained with a MyoD lentivirus were very similar. More than 30% of MyoD-hMADS cells transduced with a MOI 30 were systematically found positive for CD56, while this percentage was only ~2% for WT-hMADS cells. Thereafter, the fusion potential of MCM1-MyoD hESCs was verified by transferring them in the differentiation medium. Most of these cells expressed MHC and formed large multinucleated myotubes containing up to 20 nuclei (FIG. 8A-D). 60% of the cells were MHC positive after 7 days in differentiation medium (FIG. 8F). Moreover, the percentage of MHC positive cells was not significantly different that that observed with real human myoblasts primary cultures. Thus, the two-step approach described herein induces a high myogenic conversion of hESCs. The karyotypes of MCM1-hESCs and MCM1-MyoD-hESCs did not show abnormalities (FIGS. 9C and D).

Example 9

Myogenic Conversion of hIPSCs

Having established a 2 steps procedure for the myogenic conversion of hESCs, we applied exactly the same differentiation protocol to hiPSCs derived from a DMD patient skin fibroblast. These hiPSCs were transferred to MCM1 medium, infected with Ad.CAGMyoD and transferred to the DMEM medium with 2% FBS. We investigated the in vitro differentiation by MHC expression. As expected, 60% of the MCM1-MyoD-hiPSCs became MHC positive as observed with MCM1-MyoD-hESCs and no significant difference was observed with real human myoblasts (FIG. 8F). However, despite the fact that percentage of MHC was the same, larger myotubes were observed with dystrophic MCM1-MyoD-hiPSCs than with MCM1-MyoD-hESCs (FIG. 8E). Moreover, the karyotypes of MCM1-hiPSCs and MCM1-MyoD-hiPSCs were normal (FIGS. 9E and F).

Example 10

Cell Transplantion of hESCs or Dystrophic hiPCs Cultured in MCM1

1St Transplantation Experiment without Cardiotoxin.

Figure 10:
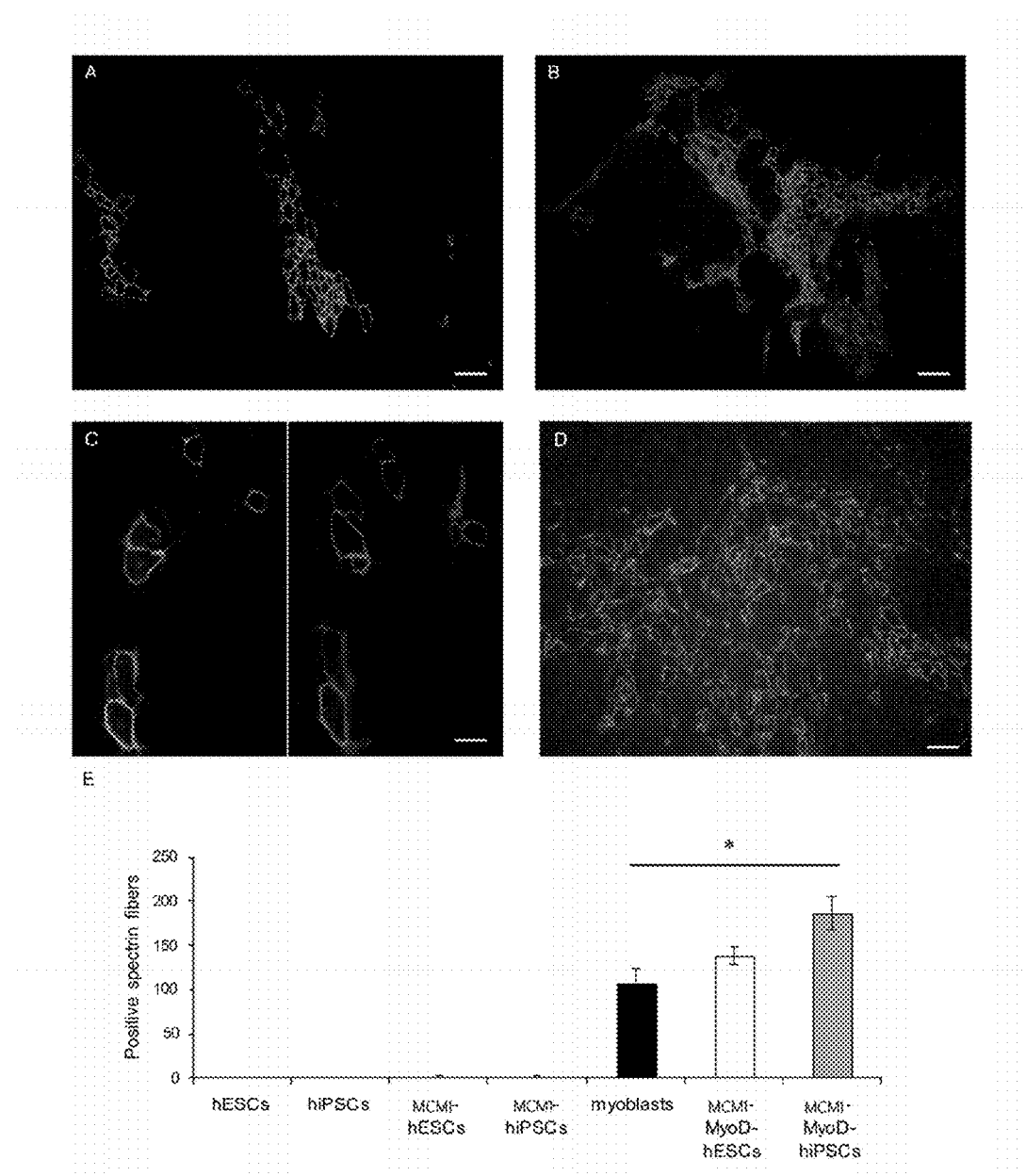
FIG. 10 shows an Immunofluorescence analysis showing human spectrin (or dystrophin) positive myofibers after transplantation in Rag/mdx mice. Representative cross-sections of Rag/mdx TA muscles injected intramuscularly with MCM1-MyoD-hESCs.

As MyoD expression confers to hESCs and to dystrophic hiPSCs the interesting myogenic capacity observed in vitro, we studied whether these infected cells might participate in muscle regeneration more efficiently than non-infected cells. We initially tested this hypothesis by transplanting 500,000 MCM1-MyoD-hESCs, 500,000 dystrophic MCM1-MyoD-hiPSCs or 500,000 human myoblasts each in the muscles of 2 rag/mdx mice. The muscles were injected at several sites (10-15) throughout the muscles. The muscles injected with cells were collected 4 weeks later. The presence of hybrid fibers resulting from the fusion of the human cells with the mouse fibers was investigated by the expression of human spectrin, a gene specifically expressed in the muscle fibers. Human spectrin was clearly detected at the membrane of many fibers but only following the transplantation of human myoblasts, MCM1-MyoD-hESCs (FIG. 10A) or MCM1-MyoD-hiPSCs (FIG. 7B). The presence of MCM1-MyoD-hESCs derived muscle fibers was further confirmed by the co labelling of most of the human spectrin-positive fibers with human specific anti dystrophin (FIG. 10C). The muscle fibers expressing human spectrin or human dystrophin were often disposed along more or less linear regions probably close to the injection trajectories. These fibers ranged from very small to large diameters. The proportion of large fibers was variable. We have often made the same observation following the transplantation of primary culture myoblasts. Expression of human spectrin by these muscles clearly demonstrates the ability of these cells to fuse with myoblasts in vivo.

2Nd Transplantation Experiment with Cardiotoxin

The implanted cells fused essentially with the myofibers near the injection trajectories, which could be due to the low number of spontaneously regenerating myofibers present at the time of transplantation in mdx mice. We thus further tested the in vivo myogenic capacity of the cells derived from hESCs and hiPSCs by transplanting different types of cells (i.e. hESCs, MCM1-hESCs, MCM1-MyoD-hESCs, dystrophic hiPSCs, MCM1-hiPSCs and MCM1-MyoD-hiPSCs) in the Tibialis anterior (TA) muscles of immunodeficient Rag/mdx mice. For this second experiment, each type of cells was co-injected with cardiotoxin in 7 muscles. The cardiotoxin was used to damage the muscle fibers of the host mice and thus permit the fusion of the transplanted cells with more host muscle fibers. Human myoblasts were again used as a positive control. The muscles injected with cells were also collected 4 weeks later. As for the previous experiment, the success of these transplantations was determined by immuno-labelling the muscle cross-section for human spectrin. As much as 500 spectrin positive fibers were observed in TA grafted either with MCM1-MyoD-hESCs or with MCM1-MyoD-hiPSCs (FIG. 10D). Human spectrin labelling was used to quantify the success of the transplantation (FIG. 10E). The total number of human spectrin-positive fibers was definitively higher following the transplantation of MCM1-MyoD-hESCs than with wild type hESCs or MCM1-hESCs. Surprisingly, the total number of human spectrin-positive fibers was higher with MCM1-MyoD-hiPSCs than with MCM1-MyoD-hESCs. Moreover, the total number of human spectrin-positive myofibers was respectively 37% and 74% higher with MCM1-MyoD-hESCs (p=0.086) and MCM1 MyoD-hIPSCs (p<0.01) than in muscles injected with the same number of control human myoblasts.

Example 11

Immuno-Labelling of the Muscle Section for Human Lamin A/C

Figure 11:
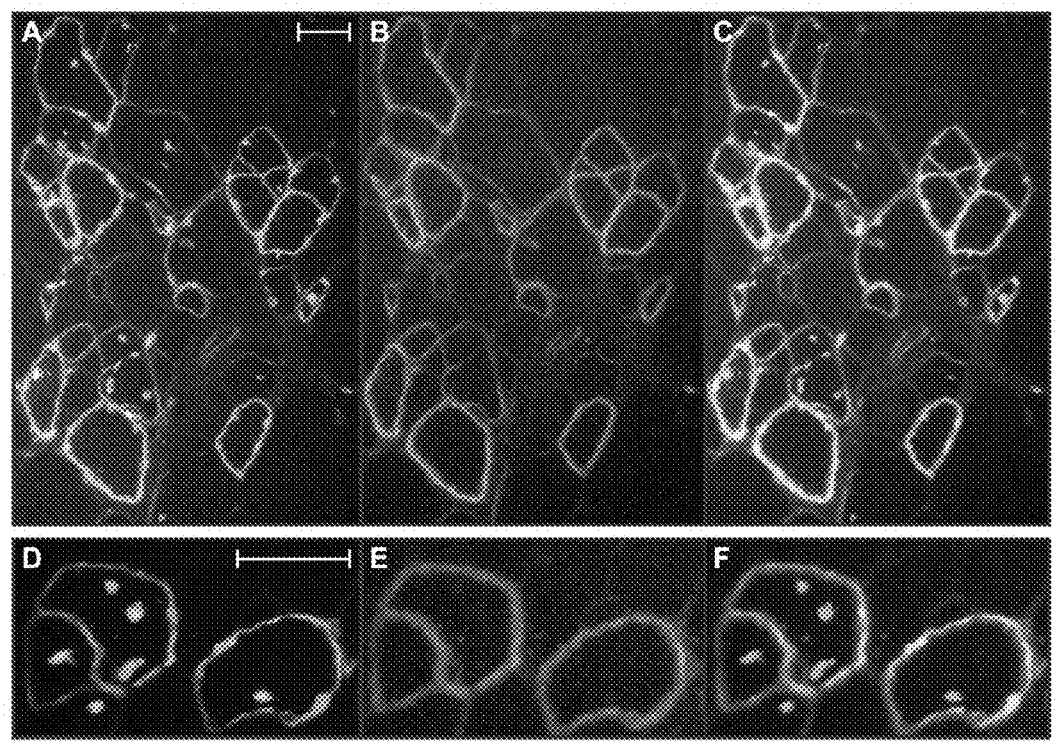
FIG. 11 shows Lamin A/C staining of muscles. Sections of rag/mdx muscles transplanted with MCM1-MyoD-hESCs were immuno-stained with an antibody to human lamin A/C (fluorescence in A and D) and for human dystrophin (fluorescence in B and E). The lamin and dystrophin fluorescences were superposed in C and F. The figure clearly illustrates that abundant human nuclei were present inside the dystrophin positive muscle fibers and in close apposition to the muscle fibers. The scale bars are 50 µm, the scale in A also applied to B and C while the scale in D also applies to E and F.

Human nuclei were identified in the sections of muscles transplanted with cells in the two experiments above by immunostaining for human lamin A/C (FIG. 11). Following the transplantation of mcm1-MyoD-hESCs, abundant human nuclei were located inside the muscle fibers expressing human dystrophin. Some human nuclei were outside the muscle fibers in a position similar to that of satellite cells. In fact, we have previously demonstrated that human myoblasts transplanted in mouse muscles formed satellite cells. This observation suggests that myogenic cells derived from hESCs may also form satellite cells. A few mcm1-MyoD-hESCs cells were also located away from the muscle fibers (as observed when we transplant human myoblasts derived from primary muscle culture).

Example 12

Absence of Teratoma in the Muscles Transplanted with hESCs and hIPSCs or with hESCs and hiPSCs Derived Cells It is important to note that no teratoma and no abnormal structure were detected in any of the muscles both in the first and in the second series of transplantation. In addition, following immuno-labelling for human lamin A/C, we did not observe any human nuclei in the sections of muscles transplanted with any type of cells. This suggests that pluripotent stem cells did not survive either to the transplantation procedure. Indeed, the hESCs and hiPSCs may be sensitive to the pressure used for the intramuscular injection, to cardiotoxin or to the highly inflammatory environment produced by the damage to the muscle fibers induced by cardiotoxin. An additional hypothesis to account for the absence of teratoma following the transplantation of cells grown in MCM1 is that the pluripotent stem cells differentiated in the MCM1 medium, but were not able to survive as pluripotent cells in this medium.

As opposed to single cells hESC growth, the proliferation of cells grown in MCM1 medium is very fast (more than myoblasts) and the level of cell death is very low. Furthermore, the myogenic differentiation is complete. Our results indicate that the combination of MCM1 medium and adenovirus is useful tool for hESC differentiation and that Ad.CAG-MyoD infection is an effective technique to differentiate hESC into skeletal muscle cells. These cells (hESCs or induced pluripotent stem cells (IPS)) can be used as an alternative source of mesenchymal cells for basic applications and for transplantation of myogenic cells for muscle repair as demonstrated in the Rag/mdx mice model.

Although the present invention has been described hereinabove by way of specific embodiments thereof, it can be modified, without departing from the spirit and nature of the subject invention as defined in the appended claims.

REFERENCES

1. Thomson, J. A., et al. (1998). Embryonic stem cell lines derived from human blastocysts. Science 282: 1145-1147.
2. Trounson, A. (2006). The production and directed differentiation of human embryonic stem cells. Endocr Rev 27: 208-219.
3. Partridge, T. A., Morgan, J. E., Coulton, G. R., Hoffman, E. P., and Kunkel, L. M. (1989). Conversion of mdx myofibres from dystrophin-negative to -positive by injection of normal myoblasts. Nature 337: 176-179.
4. Skuk, D., et al. (2007). First test of a "high-density injection" protocol for myogenic cell transplantation throughout large volumes of muscles in a Duchenne muscular dystrophy patient: eighteen months follow-up. Neuromuscul Disord 17: 38-46.
5. Zhu, S., et al. (2009). A small molecule primes embryonic stem cells for differentiation. Cell Stem Cell 4: 416-426.
6. Barberi, T., Bradbury, M., Dincer, Z., Panagiotakos, G., Socci, N. D., and Studer, L. (2007). Derivation of engraftable skeletal myoblasts from human embryonic stem cells. Nat Med 13: 642-648.
7. Ozasa, S., et al. (2007). Efficient conversion of ES cells into myogenic lineage using the gene-inducible system. Biochem Biophys Res Commun 357: 957-963.
8. Darabi, R., et al. (2008). Functional skeletal muscle regeneration from differentiating embryonic stem cells. Nat Med 14: 134-143.
9. Sassoon, D., et al. (1989). Expression of two myogenic regulatory factors myogenin and MyoD1 during mouse embryogenesis. Nature 341: 303-307.
10. Berkes, C. A., and Tapscott, S. J. (2005). MyoD and the transcriptional control of myogenesis. Semin Cell Dev Biol 16: 585-595.
11. Shani, M., Faerman, A., Emerson, C. P., Pearson-White, S., Dekel, I., and Magal, Y. (1992). The consequences of a constitutive expression of MyoD1 in ES cells and mouse embryos. Symp Soc Exp Biol 46: 19-36.
12. Weintraub, H., et al. (1989). Activation of muscle-specific genes in pigment, nerve, fat, liver, and fibroblast cell lines by forced expression of MyoD. Proc Natl Acad Sci USA 86: 5434-5438.
13. Goudenege, S., et al. (2009). Enhancement of Myogenic and Muscle Repair Capacities of Human Adipose-derived Stem Cells With Forced Expression of MyoD. Mol Ther.
14. Watanabe, K., et al. (2007). A ROCK inhibitor permits survival of dissociated human embryonic stem cells. Nat Biotechnol 25: 681-686.

15. Seale, P., Sabourin, L. A., Girgis-Gabardo, A., Mansouri, A., Gruss, P., and Rudnicki, M. A. (2000). Pax7 is required for the specification of myogenic satellite cells. *Cell* 102: 777-786.
16. Kuang, S., and Rudnicki, M. A. (2008). The emerging biology of satellite cells and their therapeutic potential. *Trends Mol Med* 14: 82-91.
17. Eiges, R. (2006). Genetic manipulation of human embryonic stem cells by transfection. In *Human embryonic stem cell protocols* (K. Turksen, Ed.), pp. 221-240. Human Press Inc, New Jersey.
18. Smith-Arica, J. R., Thomson, A. J., Ansell, R., Chiorini, J., Davidson, B., and McWhir, J. (2003). Infection efficiency of human and mouse embryonic stem cells using adenoviral and adeno-associated viral vectors. *Cloning Stem Cells* 5: 51-62.
19. Brokhman, I., et al. (2009). Genetic modification of human embryonic stem cells with adenoviral vectors: differences of infectability between lines and correlation of infectability with expression of the coxsackie and adenovirus receptor. *Stem Cells Dev* 18: 447-456.
20. Sorrentino, V., Pepperkok, R., Davis, R. L., Ansorge, W., and Philipson, L. (1990). Cell proliferation inhibited by MyoD1 independently of myogenic differentiation. *Nature* 345: 813-815.
21. Fujii, I., Matsukura, M., Ikezawa, M., Suzuki, S., Shimada, T., and Miike, T. (2006). Adenoviral mediated MyoD gene transfer into fibroblasts: myogenic disease diagnosis. *Brain Dev* 28: 420-425.
22. Zheng, J. K., et al. (2006). Skeletal myogenesis by human embryonic stem cells. *Cell Res* 16: 713-722.
23. Itskovitz-Eldor, J., et al. (2000). Differentiation of human embryonic stem cells into embryoid bodies compromising the three embryonic germ layers. *Mol Med* 6: 88-95.
24. Kablar, B., Krastel, K., Ying, C., Asakura, A., Tapscott, S. J., and Rudnicki, M. A. (1997). MyoD and Myf-5 differentially regulate the development of limb versus trunk skeletal muscle. *Development* 124: 4729-4738.
25. Gensch, N., Borchardt, T., Schneider, A., Riethmacher, D., and Braun, T. (2008). Different autonomous myogenic cell populations revealed by ablation of Myf5-expressing cells during mouse embryogenesis. *Development* 135: 1597-1604.
26. Rudnicki, M. A., Schnegelsberg, P. N., Stead, R. H., Braun, T., Arnold, H. H., and Jaenisch, R. (1993). MyoD or Myf-5 is required for the formation of skeletal muscle. *Cell* 75: 1351-1359.
27. Rudnicki, M. A., Braun, T., Hinuma, S., and Jaenisch, R. (1992). Inactivation of MyoD in mice leads to up-regulation of the myogenic HLH gene Myf-5 and results in apparently normal muscle development. *Cell* 71: 383-390.
28. Giordani, J., Bajard, L., Demignon, J., Daubas, P., Buckingham, M., and Maire, P. (2007). Six proteins regulate the activation of Myf5 expression in embryonic mouse limbs. *Proc Natl Acad Sci USA* 104: 11310-11315.
29. Kitzmann, M., Carnac, G., Vandromme, M., Primig, M., Lamb, N. J., and Fernandez, A. (1998). The muscle regulatory factors MyoD and myf-5 undergo distinct cell cycle-specific expression in muscle cells. *J Cell Biol* 142: 1447-1459.
30. Collins, C. A., et al. (2009). Integrated functions of Pax3 and Pax7 in the regulation of proliferation, cell size and myogenic differentiation. *PLoS ONE* 4: e4475.
31. Olguin, H. C., and Olwin, B. B. (2004). Pax-7 up-regulation inhibits myogenesis and cell cycle progression in satellite cells: a potential mechanism for self-renewal. *Dev Biol* 275: 375-388.
32. Zammit, P. S., Golding, J. P., Nagata, Y., Hudon, V., Partridge, T. A., and Beauchamp, J. R. (2004). Muscle satellite cells adopt divergent fates: a mechanism for self-renewal? *J Cell Biol* 166: 347-357.
33. Halevy, O., et al. (2004). Pattern of Pax7 expression during myogenesis in the posthatch chicken establishes a model for satellite cell differentiation and renewal. *Dev Dyn* 231: 489-502.
34. Tapscott, S. J., and Weintraub, H. (1991). MyoD and the regulation of myogenesis by helix-loop-helix proteins. *J Clin Invest* 87: 1133-1138.
35. Ludwig, T E, Bergendahl, V, Levenstein, M E, Yu, J, Probasco, M D, and Thomson, JA (2006). Feeder-independent culture of human embryonic stem cells. Nat Methods 3: 637-646.
36. Park, I H, et al. (2008). Disease-specific induced pluripotent stem cells. Cell 134: 877-886.
37. Fujii, I, Matsukura, M, Ikezawa, M, Suzuki, S, Shimada, T, and Miike, T (2006). Adenoviral mediated MyoD gene transfer into fibroblasts: myogenic disease diagnosis. Brain Dev 28: 420-425.
38. Huard, J, Tremblay, G, Verreault, S, Labrecque, C, and Tremblay, J P (1993). Utilization of an antibody specific for human dystrophin to follow myoblast transplantation in nude mice. Cell Transplant 2: 113-118.
39. Rando, T A, and Blau, H M (1994). Primary mouse myoblast purification, characterization, and transplantation for cell-mediated gene therapy. J Cell Biol 125: 1275-1287.
40. Benabdallah, B F, et al. (2008). Inhibiting myostatin with follistatin improves the success of myoblast transplantation in dystrophic mice. Cell Transplant 17: 337-350.

---

The invention claimed is:

1. A method of inducing differentiation of human induced pluripotent stem cells (iPSCs) into myogenic cells comprising i) culturing said iPSCs in a myogenic differentiation medium to induce differentiation into mesenchymal-like cells expressing TBX1 and TBX4; and ii) culturing said mesenchymal-like cells in the presence of at least one myogenic factor to complete differentiation into myogenic cells.

2. The method of claim 1, wherein said myogenic differentiation medium comprises basic fibroblast growth factor (bFGF) and/or insulin.

3. The method of claim 2, further comprising first growing said iPSCs in a proliferation medium.

4. The method of claim 3, wherein said proliferation medium comprises between about 10 and about 30% of serum.

5. The method of claim 3, wherein said myogenic differentiation medium and said proliferation medium are substantially the same as Myogenic Culture Medium 1 (MCM1).

6. The method of claim 5, wherein said iPSCs are CD73 positive cells.

7. The method of claim 6, wherein the presence of said at least one myogenic factor is provided by:
   i) Treating said iPSCs with at least one myogenic factor protein;
   ii) Inducing said at least one myogenic factor expression in said iPSCs; or
   iii) Introducing in said iPSCs at least one nucleic acid capable of expressing said at least one myogenic factor.

8. The method of claim 7, wherein said at least one myogenic factor is MyoD, Pax3, Pax7, Myf5 or myogenin.

9. The method of claim 8, wherein said at least one myogenic factor is MyoD.

10. The method of claim 9, wherein said MyoD is provided by introducing in said iPSCs a nucleic acid sequence capable of expressing MyoD.

11. The method of claim 10, wherein said MyoD is introduced in said iPSCs with an adeno-associated viral vector; a retroviral vector, a lentiviral vector, a non-integrative lentiviral vector or a non-viral vector.

12. The method of claim 11, comprising growing said iPSCs as single cells.

13. The method of claim 12, wherein said myogenic cells express at least one of the following myogenic markers: Pax7, MyoD, myogenin, CD56, desmin and MHC and express low levels of Rex-1.

14. The method of claim 2, wherein said myogenic differentiation medium comprises between about 0.5 and about 2% of serum.

15. The method of claim 2, wherein said myogenic differentiation medium comprises between about 0.5% and about 5% of serum.

16. The method of claim 1, wherein said iPSCs are derived from a fibroblast of a Duchenne muscular dystrophy patient.

17. A method of transplanting myogenic cells in a subject comprising implanting in said subject myogenic cells prepared by i) culturing human induced pluripotent stem cells (iPSCs) in a myogenic differentiation medium to induce differentiation into mesenchymal-like cells expressing TBX1 and TBX4; and ii) culturing said mesenchymal-like cells in the presence of a myogenic factor to complete differentiation into myogenic cells.

18. The method of claim 17, wherein said transplantation is for increasing muscle mass in a subject suffering from Duchenne muscular dystrophy.

19. The method of claim 17, wherein said myogenic differentiation medium is substantially the same as Myogenic Culture Medium 1 (MCM1).

* * * * *